(12) United States Patent
Soong et al.

(10) Patent No.: US 6,959,589 B1
(45) Date of Patent: Nov. 1, 2005

(54) ULTRASOUND ANALYSIS OF SLURRIES

(75) Inventors: Yee Soong, Monroeville, PA (US); Arthur G. Blackwell, Duquesne, PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/677,238

(22) Filed: Oct. 3, 2003

(51) Int. Cl.⁷ .................. G01N 15/06; G01N 29/02; G01N 29/24
(52) U.S. Cl. .............. 73/61.75; 73/61.71; 73/596; 73/618; 73/624; 73/632
(58) Field of Search ............ 73/61.71, 61.75, 73/584, 596, 618, 624, 632

(56) References Cited

U.S. PATENT DOCUMENTS

| | | | |
|---|---|---|---|
| 4,527,420 A | 7/1985 | Foote et al. | 73/61.75 |
| 4,567,765 A * | 2/1986 | Rao et al. | 73/594 |
| 4,580,444 A | 4/1986 | Abts et al. | 73/61.75 |
| 4,770,042 A | 9/1988 | Cobb et al. | 73/597 |
| 4,770,043 A | 9/1988 | Cobb et al. | 73/597 |
| 5,058,432 A | 10/1991 | Mokun et al. | 73/599 |
| 5,936,163 A * | 8/1999 | Greathouse | 73/644 |
| 5,992,223 A * | 11/1999 | Sabins et al. | 73/64.42 |
| 6,039,059 A * | 3/2000 | Bran | 134/105 |

* cited by examiner

*Primary Examiner*—Daniel S. Larkin
(74) *Attorney, Agent, or Firm*—Brian J. Lally; Daniel D. Park; Paul A. Gottlieb

(57) ABSTRACT

An autoclave reactor allows for the ultrasonic analysis of slurry concentration and particle size distribution at elevated temperatures and pressures while maintaining the temperature- and pressure-sensitive ultrasonic transducers under ambient conditions. The reactor vessel is a hollow stainless steel cylinder containing the slurry which includes a stirrer and a $N_2$ gas source for directing gas bubbles through the slurry. Input and output transducers are connected to opposed lateral portions of the hollow cylinder for respectively directing sound waves through the slurry and receiving these sound waves after transmission through the slurry, where changes in sound wave velocity and amplitude can be used to measure slurry parameters. Ultrasonic adapters connect the transducers to the reactor vessel in a sealed manner and isolate the transducers from the hostile conditions within the vessel without ultrasonic signal distortion or losses.

19 Claims, 25 Drawing Sheets

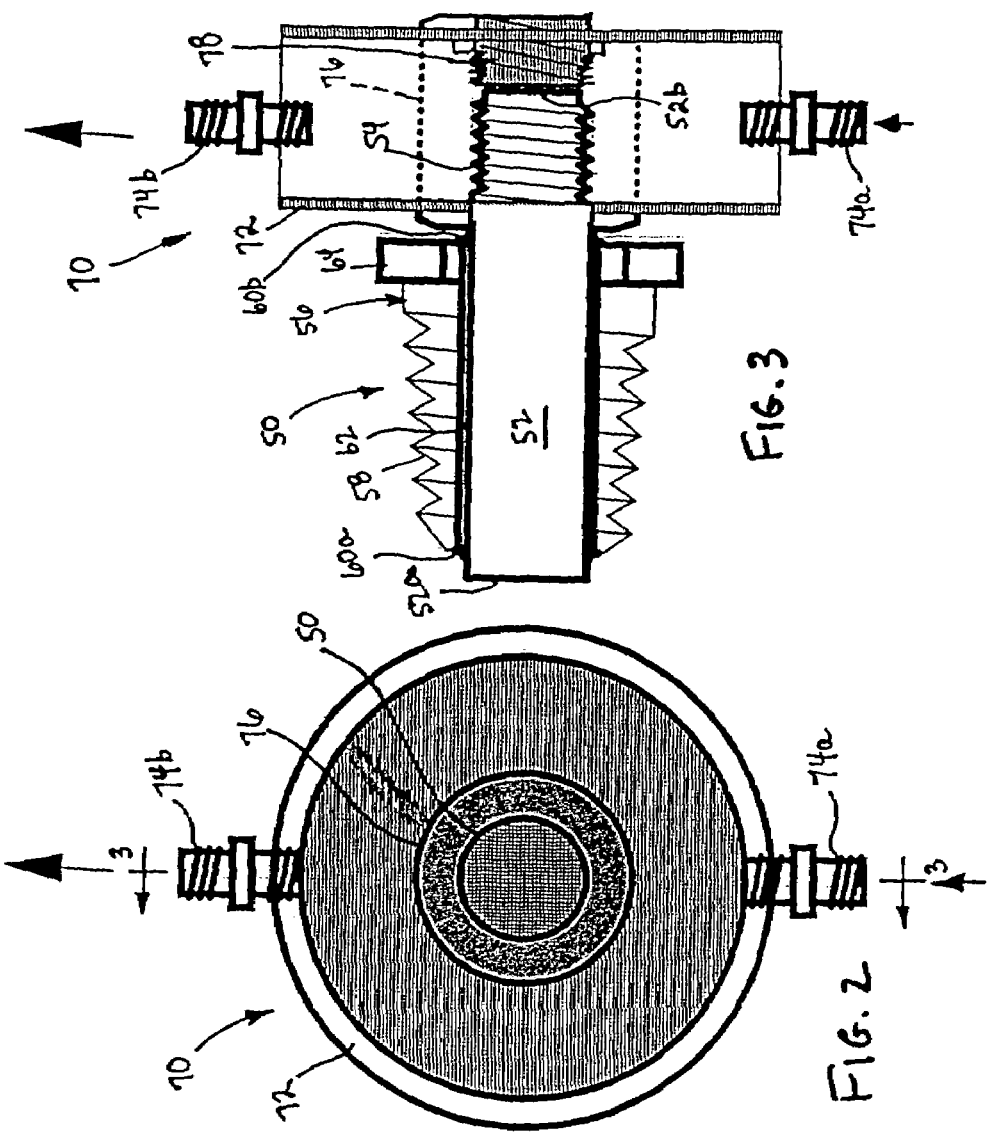

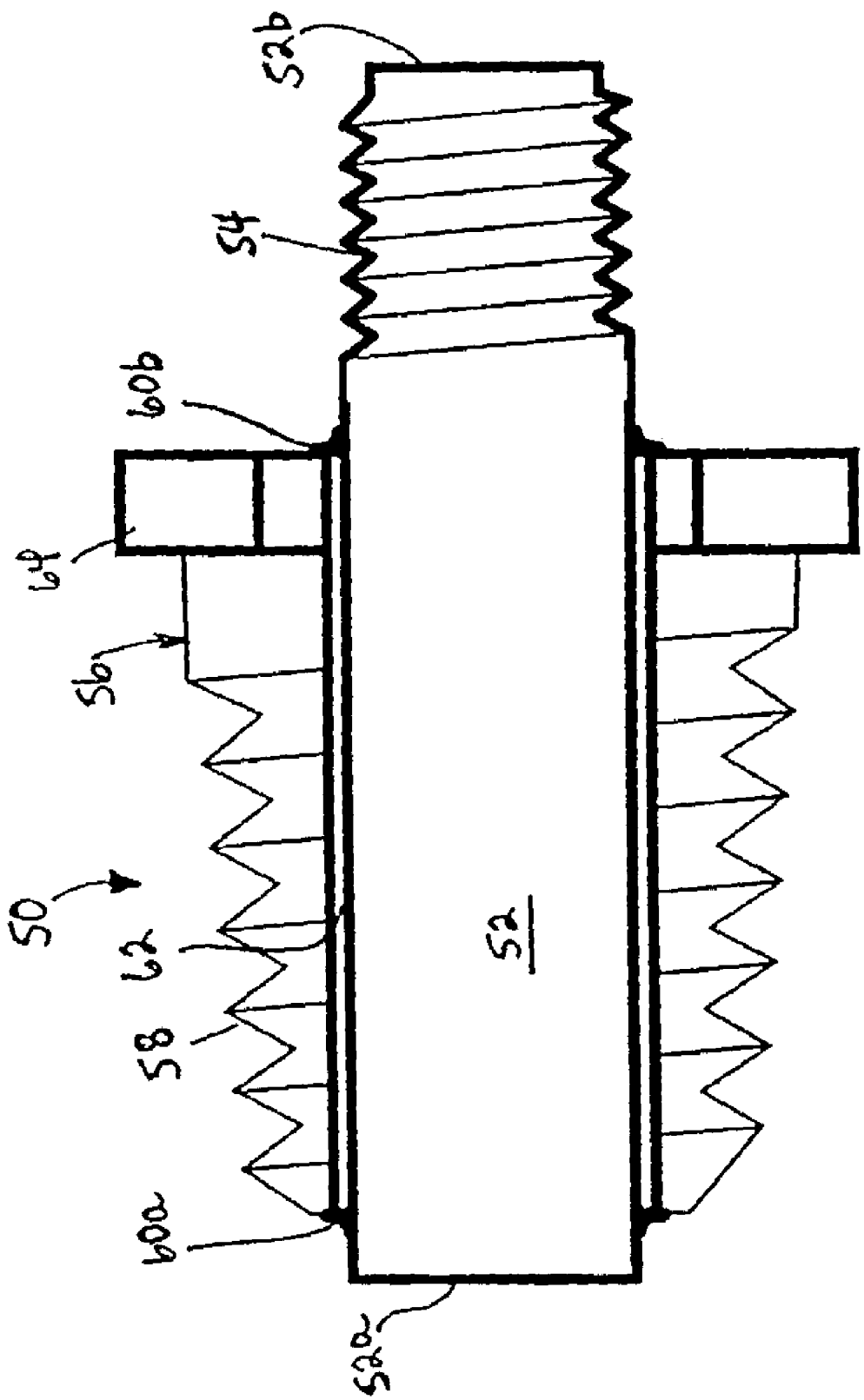

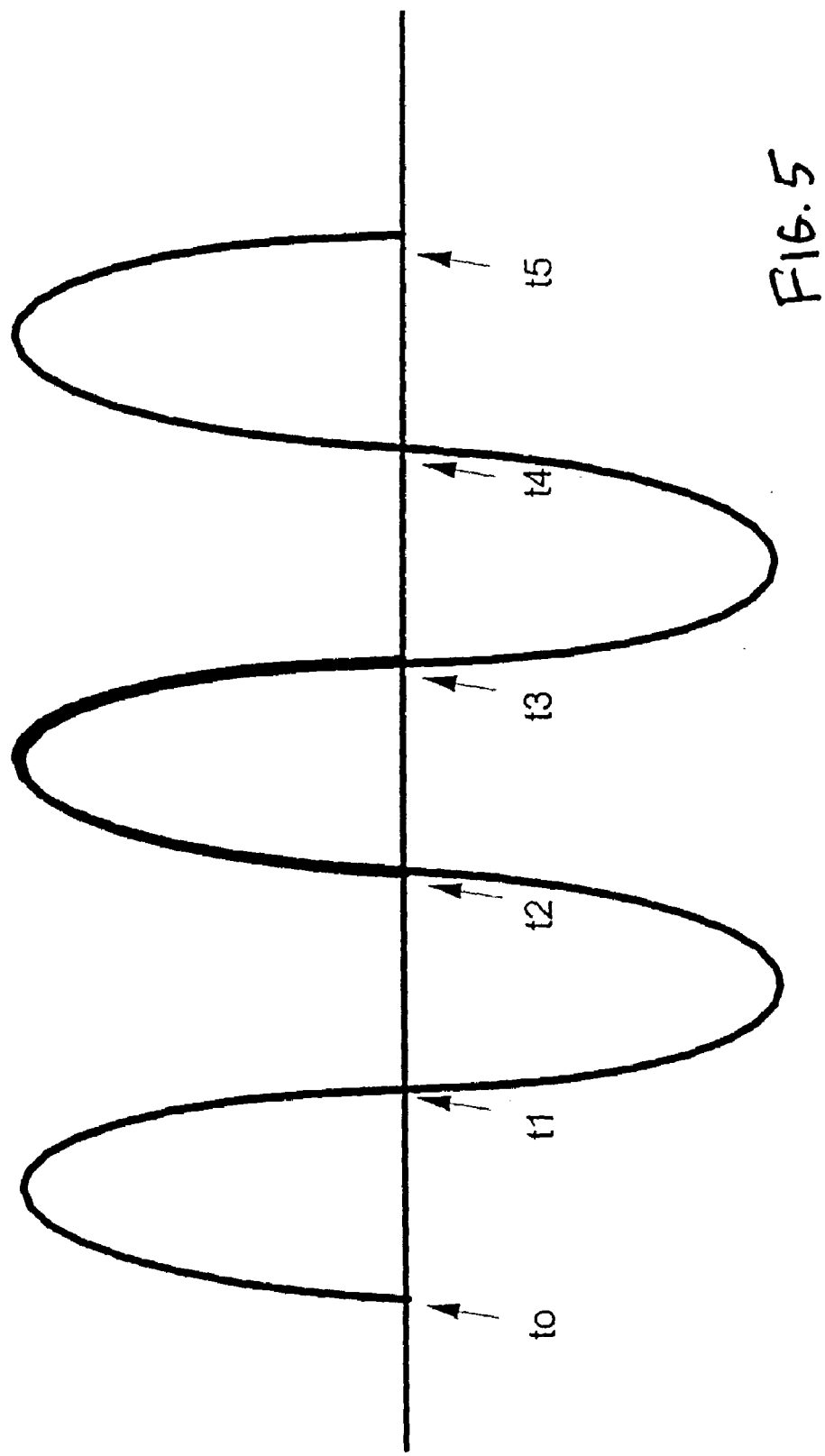

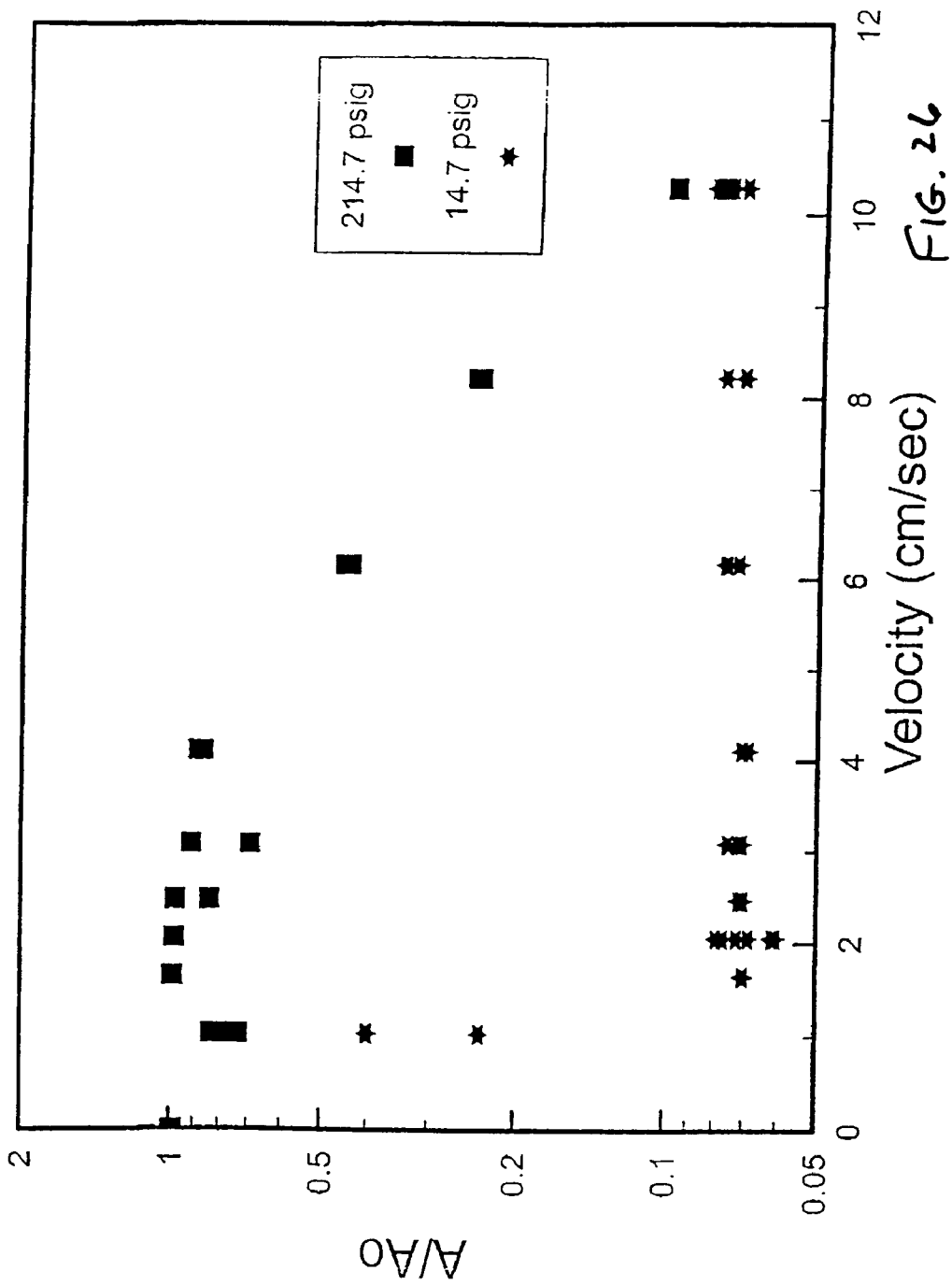

ULTRASOUND ANALYSIS OF SLURRIES

CONTRACTUAL ORIGIN OF THE INVENTION

The United States Government has rights in this invention pursuant to Contract No. W-31-109-ENG-38 between the U.S. Department of Energy and the University of Chicago.

FIELD OF THE INVENTION

This invention relates generally to apparatus for analyzing materials in slurry form and is particularly directed to an autoclave arrangement for determining the concentration and/or particle size distribution of a slurry under elevated temperature and pressure conditions.

BACKGROUND OF THE INVENTION

Ultrasonic measurement is an established technique for many industrial applications, such as in medical imaging, materials testing, flow detection and level measurements. The ultrasonic technique has advantages over many existing methods because it is a noninvasive and nondestructive measurement of systems which are concentrated, optically opaque and electrically nonconducting. The primary limitation of this ultrasonic measurement technique has been in its use of its ultrasonic transducers which cannot operate in high temperature and high pressure environments. Some known ultrasonic measurement techniques are briefly discussed in the following paragraphs.

U.S. Pat. No. 4,580,444 to Abts et al. discloses an ultrasonic technique to determine the concentration of oil droplets in an oil recovery system by detecting the forward scattering of ultrasonic energy from oil droplets in the oil recovery system. This technique can only be used under ambient conditions and cannot be used at elevated temperatures and pressures.

U.S. Pat. No. 4,527,420 to Foote et al. discloses a method of identifying and determining the size of particulates in a flowing fluid comprising detecting the portion of an ultrasonic pulse scattered from particulates at a preselected angle, converting the results into density and elasticity-related values, and comparing the values with measured or computed values for known particulates. This method also can only be used under ambient conditions.

U.S. Pat. Nos. 4,770,042 and 4,770,043 to Cobb et al. disclose an apparatus for monitoring the suspension stability in a slurry. This apparatus is limited to use under ambient conditions.

U.S. Pat. No. 5,058,432 to Morkun et al. discloses a method for measuring parameters of solid phase slurries. This approach can only be used under ambient conditions.

The present invention overcomes these limitations of the prior art by positioning ultrasonic transducers outside of the high temperature and high pressure environment of the material being analyzed, while allowing for transmission of ultrasonic waves through the material for analysis of its concentration and particle size distribution. The ultrasonic measurement approach of the present invention is adapted for use in measuring the solid and gas concentrations in an autoclave reactor at elevated temperatures and pressures.

OBJECTS AND SUMMARY OF THE INVENTION

Accordingly, it is an object of the present invention to employ ultrasonic waves in the study of materials at elevated temperatures and pressures by isolating the sensitive ultrasonic system from the hostile environment of the material under study.

It is another object of the present invention to provide for the ultrasonic analysis of a slurry at high temperatures and pressures.

A further object of the present invention is to measure the concentration and particle size distribution of a slurry based upon the velocity and attenuation of sound waves directed through the slurry.

Yet another object of the present invention is to provide an autoclave reactor arrangement for use with ultrasonic transducers in the nondestructive and noninvasive measurement of the concentration and/or particle size distribution of materials, such as in slurry form, at elevated temperatures and pressures.

The present invention contemplates the use of measurements in changes of velocity (transit time) and attenuation (amplitude ratio) of sound waves traveling through a sample under investigation such as a slurry. Changes in transit time and amplitude ratio are used to determine slurry concentration and/or particle size distribution, where the slurry may be in gas and/or solid phase. The present invention allows environmentally sensitive transducers to be used with slurries maintained at temperatures above 60° C. and pressures greater than one (1) atmosphere. The transit time and amplitude ratio of the sound wave exhibits a maximum (transit time) and a minimum (amplitude ratio) relationship with the concentration of the slurry. This measurement capability makes feasible the measurement of concentration during operation of a three-phase slurry reactor under reaction temperatures and pressures. The present invention overcomes the previously encountered high temperature/pressure limitations by using a cooling chamber assembly to maintain the temperature of the transducers below 60° C., while the reactor temperature is at or exceeds 265° C. Ultrasonic adapters are used with the cooling chambers for each of the transmitting and receiving transducers to maintain atmospheric pressure on the transducer side, while the autoclave reactor side is under pressure as high as 200 psi or greater. The autoclave reaction includes a $N_2$ gas source for bubbling the gas through the slurry as well as a stirrer for mixing the slurry.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 2 is a sectional view of a coupler for connecting an ultrasound wave generating or receiving transducer to an autoclave reactor for use in the ultrasound analysis of slurries in accordance with one aspect of the present invention;

FIG. 3 is a sectional view of the coupler shown in FIG. 2 taken along sight line 3—3 therein;

FIG. 4 is a sectional view of an ultrasound adapter for use in the transducer coupler shown in FIGS. 2 and 3;

FIG. 5 is a graphic illustration of an ideal ultrasonic wave propagating in liquid as contemplated for use in the present invention;

FIG. 26 graphically illustrates the change in the amplitude ratio ($A/A_0$) of transmitted ultrasonic signals 20" above the gas distributor as a function of gas velocity under two different pressures at 20° C.

DETAILED DESCRIPTION OF THE PREFERRED EMBODIMENTS

Figure 1:
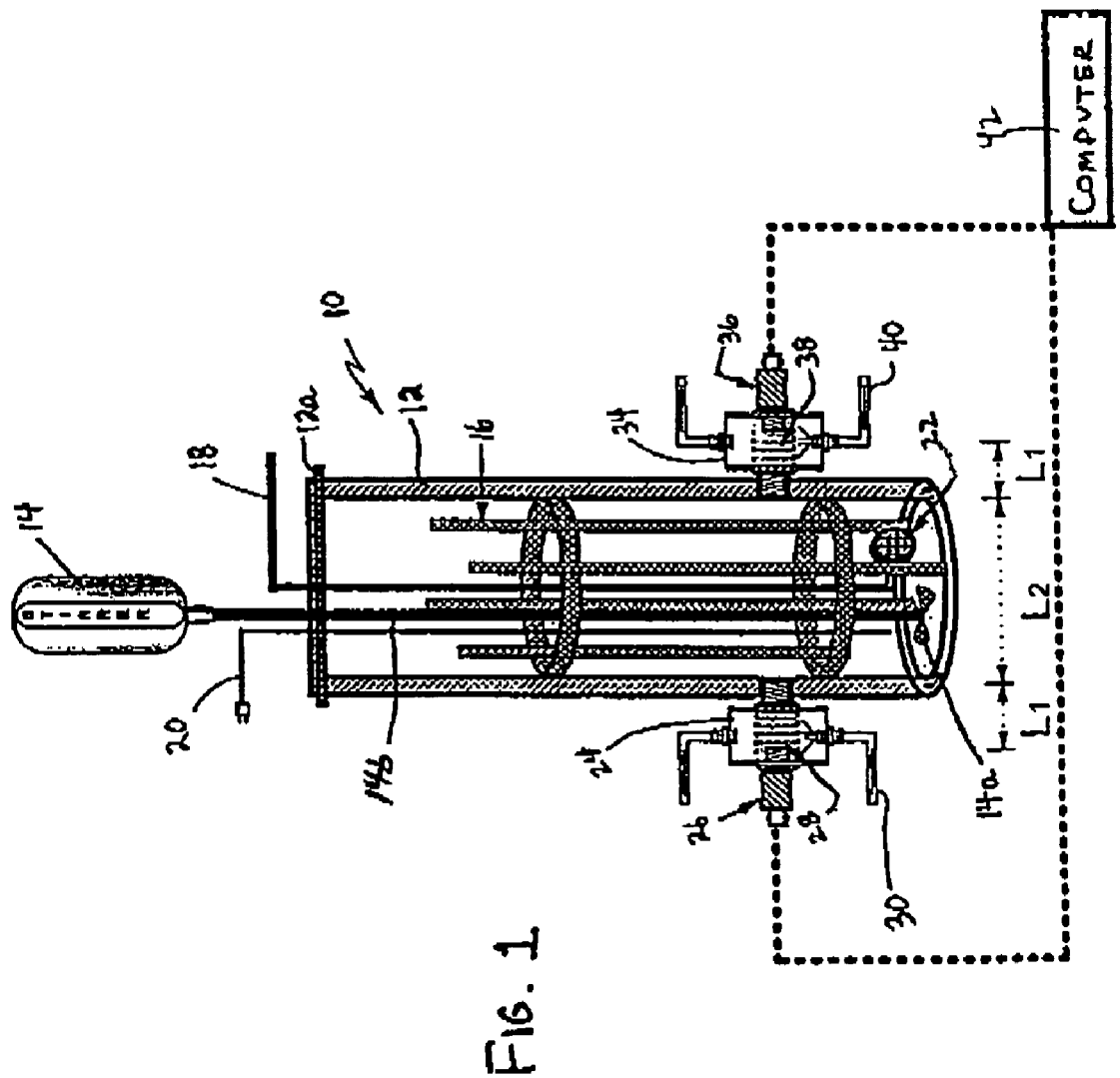
FIG. 1 is a schematic diagram of an arrangement for conducting ultrasound analysis of slurries using an autoclave reactor in accordance with one embodiment of the present invention.

Referring to FIG. 1, there is shown a schematic diagram of an arrangement for conducting ultrasound analysis of slurries in accordance with the principles of the present invention. The ultrasound analysis arrangement shown in FIG. 1 is particularly adapted for ultrasound analysis of slurries at high temperature. The ultrasound analysis arrangement includes an autoclave reactor 10 comprised of a reactor vessel 12 having a hollowed-out, generally cylindrical shape and including a cover 12a attached to the cylindrical reactor vessel in a sealed manner. Reactor vessel 12 is preferably comprised of stainless steel and in the embodiment shown in FIG. 1 is 10.6 cm. in diameter, 30 cm. in height and has a volume of 2.5 liters. Disposed within the reactor vessel 12 is the slurry being investigated. Also disposed within the reactor vessel 12 are four equally spaced, vertically baffles 16, each 1/8 of the diameter of the reactor vessel in width. Extending into the reactor vessel 12 is a stirrer 14 having one or more propeller blades 14a attached thereto for stirring the slurry. The baffles 16 increase the stirring action of the slurry within the reactor vessel 12. Also disposed within the reactor vessel 12 and extending into the slurry is a $N_2$ gas line 18 which provides $N_2$ bubbles which are discharged at the bottom of the slurry via a gas nozzle 22. The bubbles travel upward through the slurry for further increasing the stirring action on the slurry. The shaft 14b of the stirrer 14 is located slightly off center from the axis of the reactor vessel 12 to avoid interference with ultrasonic signals propagated through the slurry as described in detail below. Finally, a thermocouple lead 20 extends into the slurry within the reactor vessel 12 for measuring the temperature of the slurry.

Attached to opposed portions of the lateral wall of the reactor vessel 12 are first and second couplers 24 and 34. Attached to the first coupler 24 is a first transmitting transducer 26 which emits ultrasonic signals, or waves, which are directed through the lateral wall of the reactor vessel 12 and into the slurry. Connecting the first coupler 24 and the first transducer 26 to the reactor vessel 12 is a first adapter 28. A cooling water line 30 directs water through the first coupler 24 for maintaining the coupler, the first transducer 26 and the first adapter 28 at ambient temperature. Similarly, the combination of a second coupler 34 and a second transducer 36 is coupled to the lateral wall of the reactor vessel 12 by means of a second adapter 38. A cooling water line 40 is also connected to the second coupler 34 for allowing cooling water to flow through the coupler for maintaining the second coupler 34, the second transducer 36 and the second adapter 38 at ambient temperature. The ultrasonic measurement arrangement of FIG. 1 is computer controlled, with a computer 42 coupled to the transmitting transducer 26 as well as to the receiving transducer 36.

Referring to FIG. 2, there is shown a transverse sectional view of a coupler 70 for connecting a transducer to the reactor vessel 12 in accordance with the present invention. FIG. 3 is a sectional view of the coupler 70 shown in FIG. 2 taken along sight line 3-3 therein. FIG. 4 is a longitudinal sectional view of a portion of the coupler shown in FIGS. 2 and 3 showing additional details of an adapter 50 used to connect a transducer to the reactor vessel.

Coupler 70 is comprised of a disc-shaped, hollow cooling chamber 72, an outer, hollow, threaded adapter 50, and an inner coupling rod 52. Opposed portions of the coupler's cylindrical wall are threadably coupled to a coolant inlet connector 74a and a coolant outlet connector 74b. The inlet and outlet connectors 74a, 74b allow a coolant to be continuously circulated through cooling chamber 72 for maintaining a transducer 78 connected to the coupler at an ambient temperature. Transducer 78 is either of the ultrasonic signal transmitter type or the ultrasonic signal receiver type and is inserted through and connected to one of the generally flat end walls of the cooling chamber 72. The ultrasonic signal transmitting or receiving end of the transducer 78 is disposed within the cooling chamber 72. Extending through a second opposed flat end wall of the cooling chamber 72 is adapter 50 which is comprised of a cylindrical-shaped, inner coupling rod 52 and an outer bushing 56. The inner coupling rod 52 is inserted within and extends along the length of the outer bushing 56 and has first and second opposed ends 52a and 52b. The first end 52a of the inner coupling rod 50 is disposed within the reactor vessel 12 shown in FIG. 1, while a second, opposed end of the inner coupling rod is disposed in contact with the acoustic signal transmitting or receiving end of transducer 78. Inner coupling rod 52 includes an outer threaded end portion 54 for securely attaching the coupling rod to an insert rod 76 disposed in a tight fitting manner within the cooling chamber 72 and aligned along its central axis. The coolant circulated through the cooling chamber 72 flows around the insert rod 76, allowing heat transmitted from the reactor vessel 12 to be removed from the coupler 70 for maintaining the transducer 78 at ambient temperature. Insert rod 76 is in the form of a hollow stainless steel member having a threaded aperture extending through it along its longitudinal axis for attachment to the threaded end portion 52b of the inner coupling rod 52 and the threaded end portion of transducer 78 for maintaining the inner coupling rod and transducer in intimate, edge-abutting contact as shown in FIG. 3. Insert rod 76 also facilitates heat transfer from transducer 78 to the coolant circulated through the coupler's cooling chamber 72.

Outer bushing 56 is in the form of a hollowed-out bolt and includes a proximal tapered threaded portion 58 and a distal head portion 64. The tapered threaded portion 58 of outer bushing 56 is adapted for mating engagement with a complementary threaded aperture within the lateral wall of the reactor vessel 12 for securely connecting the adapter 50 to the reactor vessel in a sealed manner. The outer bushing's head portion 64 facilitates securely connecting the outer bushing 56 to the reactor vessel 12. Outer bushing 56 is connected to the inner coupling rod 52 by means of first and second spot weldments 60a and 60b which extend about the outer periphery of the inner coupling rod. The combination of the inner coupling rod 52, outer bushing 56, and the first and second spot weldments 60a and 60b form a closed annular cavity 62 about the outer periphery of the inner coupling rod 52. This closed annular cavity eliminates heat transfer from the wall of the reactor via the tapered threaded portion 58 of the outer bushing 56 to the inner coupling rod 52 and transducer 78 by convection and radiation. This reduced amount of heat transmitted by the inner coupling rod 52 outwardly from the reactor vessel 12 toward the transducer 78 is removed from the distal end of the inner coupling rod by the coolant circulated through coupler 70 as previously described. The small gap of the closed annular cavity 62 prevents ultrasonic signals transmitted through the wall of the reactor from reaching transducer 78 and causing ultrasonic signal interference. Coupler 70, including its cooling chamber 72 and adapter 50, are preferably comprised of stainless steel. The slurry analysis results shown graphically in FIGS. 5-23, which are described in detail below, were obtained using the autoclave reactor of FIG. 1 incorporating the coupler arrangement 70 shown in FIGS. 2, 3 and 4.

FIG. 5 illustrates an ideal ultrasonic wave propagating in liquid as in the arrangement of the present invention. Since the received signal is undistorted, the distinct zero crossing time is chosen as the transit time. Here, to is the arbitrary first distinct zero crossing time in liquid. The travel time between the transmitter and receiver in the liquid is defined as $t_o$. $t_1$ is the arbitrary second distinct zero crossing time. $t_2$, $t_3$, $t_4$, and $t_5$, are also defined as the distinct zero crossing times. The speed of sound in the liquid can be determined by utilizing the following equation and the transit time.

$$t_0 = 2L_1/V_1 + L_2/V_2 \quad (1)$$

Here, $t_0$ is the transit time defined as the first distinct zero crossing time, L, is the distance of the adapter of 3.38 cm. V, is the speed of sound travel in stainless steel at 20° C. of 5660 m/sec. $L_2$ is the distance between two adapters of 11.22 cm, and $V_2$ is the speed of sound travel in the liquid at 20° C. or conditions of interest.

Figure 6:
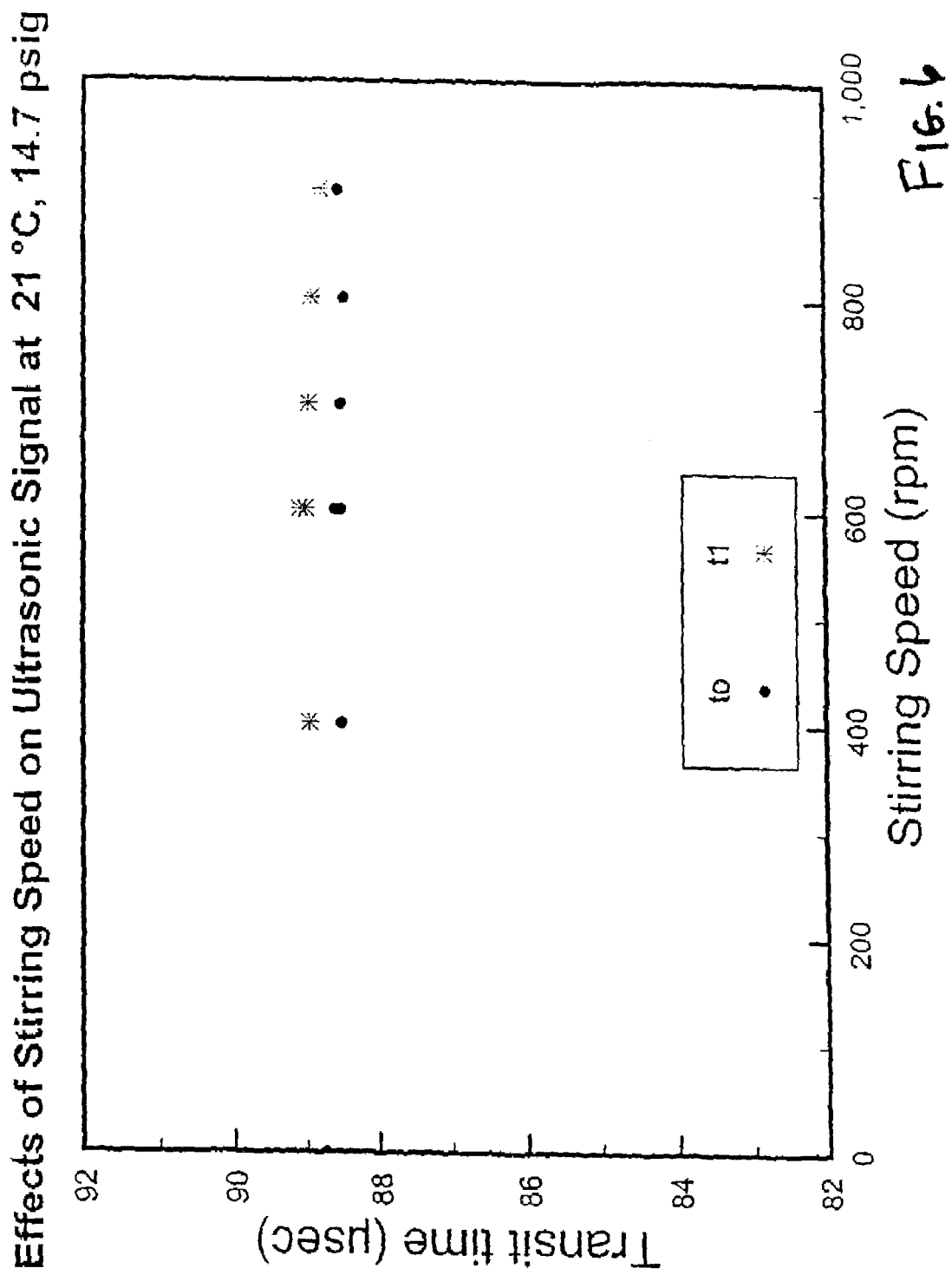
FIG. 6 graphically illustrates the change in transit times ($t_o$ and $t_1$) of a transmitted ultrasonic signal in the autoclave reactor arrangement of the present invention as a function of stirring speeds.
Figure 7:
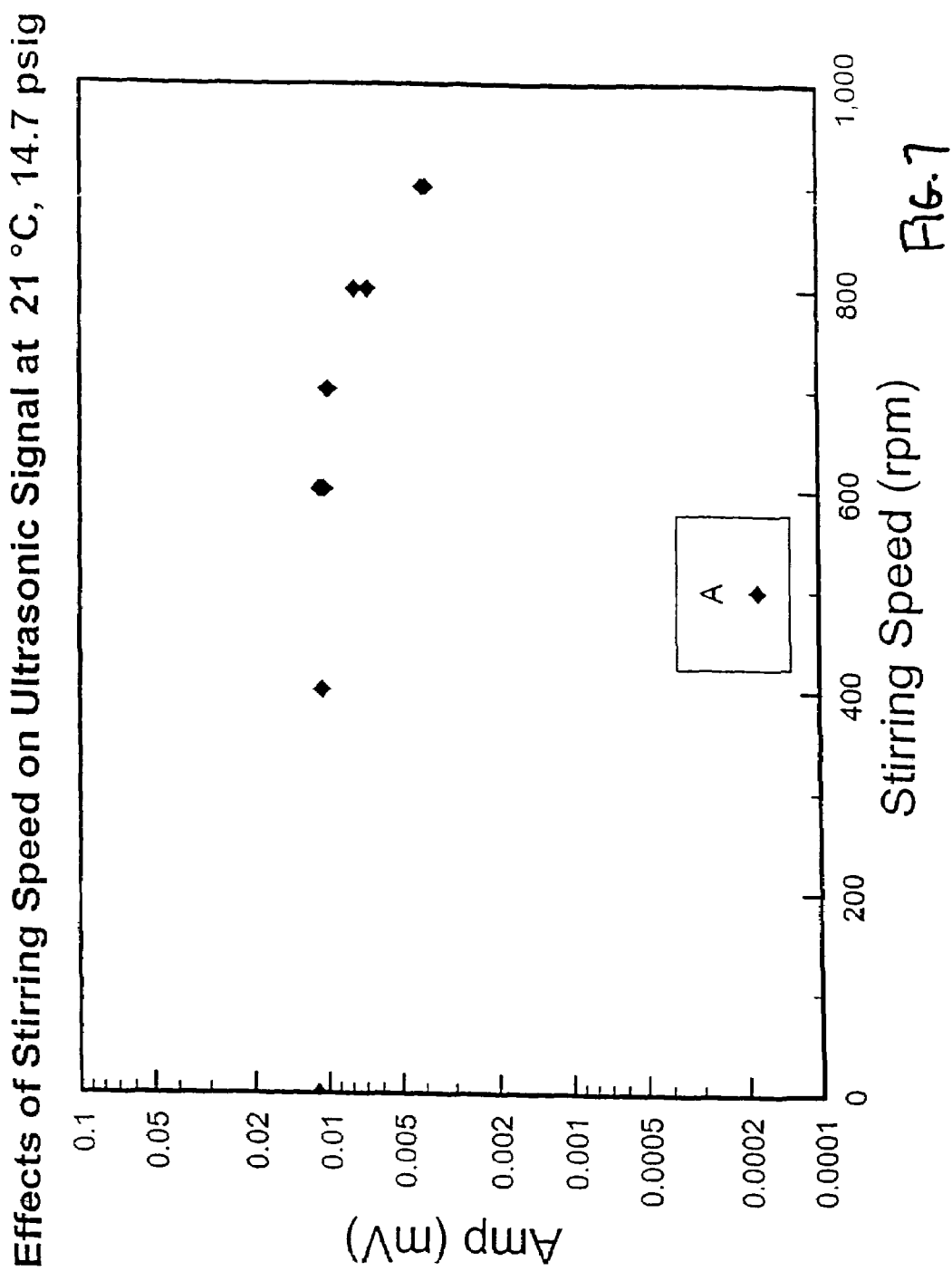
FIG. 7 is a graphic illustration of the effect of stirring speed on the amplitude of a transmitted ultrasonic signal in Therminol.

FIG. 6 shows the changes in transit times ($t_o$ and $t_1$) of the transmitted ultrasonic signal in the reactor as a function of stirring speeds in Therminol, which was used as the liquid medium, at 21° C. The transit time, $t_o$, is approximately 88.56 µs at all stirring speeds. The transit time is unaffected by the stirring speeds under the disclosed conditions. FIG. 7 further illustrates the effect of the stirring speed on the amplitude of the transmitted ultrasonic signal in Therminol at 21° C. FIG. 7 also suggests that the amplitude is independent of the stirring speeds as long as the stirring speed is 600 rpm or less. However, the amplitude decreases when the stirring speed is above 600 rpm. The amplitude of the signal obtained under 900 rpm is approximately 30 to 40% of that obtained under 600 rpm. The decrease in amplitude with increasing stirring speed is probably due to the presence of vortexes under higher stirring speed. Creating vortexes will introduce gas bubbles in the ultrasonic path that reduce the amplitude of the transmitted ultrasonic signal. To overcome this complication, the initial liquid level should be sufficiently higher than the stirrer. Most of the data in this application is shown at both 600 and 800/900 rpm.

Figure 8:
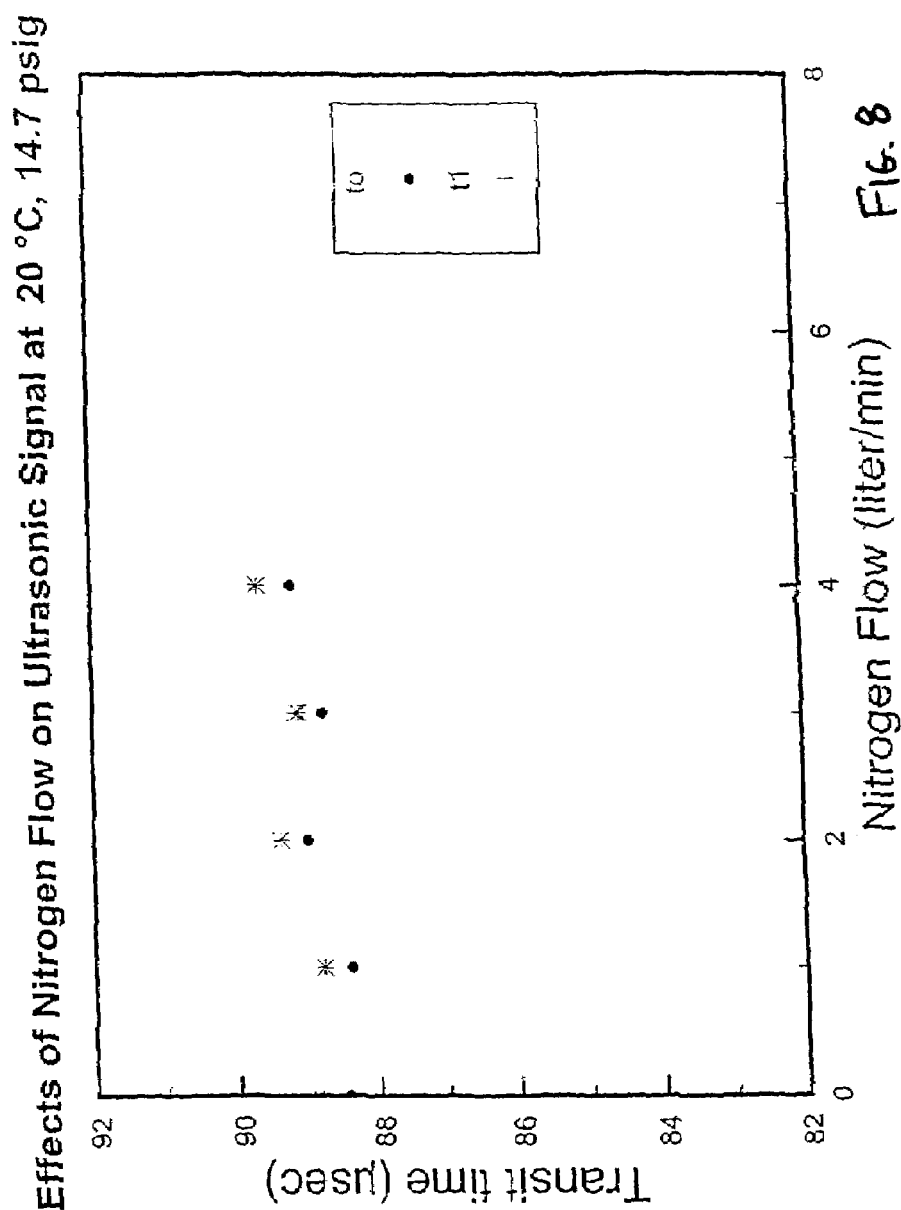
FIG. 8 is a graphic illustration of the effect of nitrogen flow on acoustic wave transit time, $t_0$, as determined by the present invention.

FIG. 8 illustrates the effect of nitrogen flow on the transit time, $t_0$. The transit time is approximately 88.76 μs at all nitrogen flows in Therminol at 600 rpm and 20° C. The transit time is unaffected by nitrogen flow under the current conditions because the signal is not transmitted through the nitrogen. Thus, the measured transit time should not be affected by nitrogen flow. The speed of sound travel through the Therminol can be determined by using $t_o$ and equation (1). The speed of sound in Therminol at 20° C. is 1467 m/sec.

Figure 9:
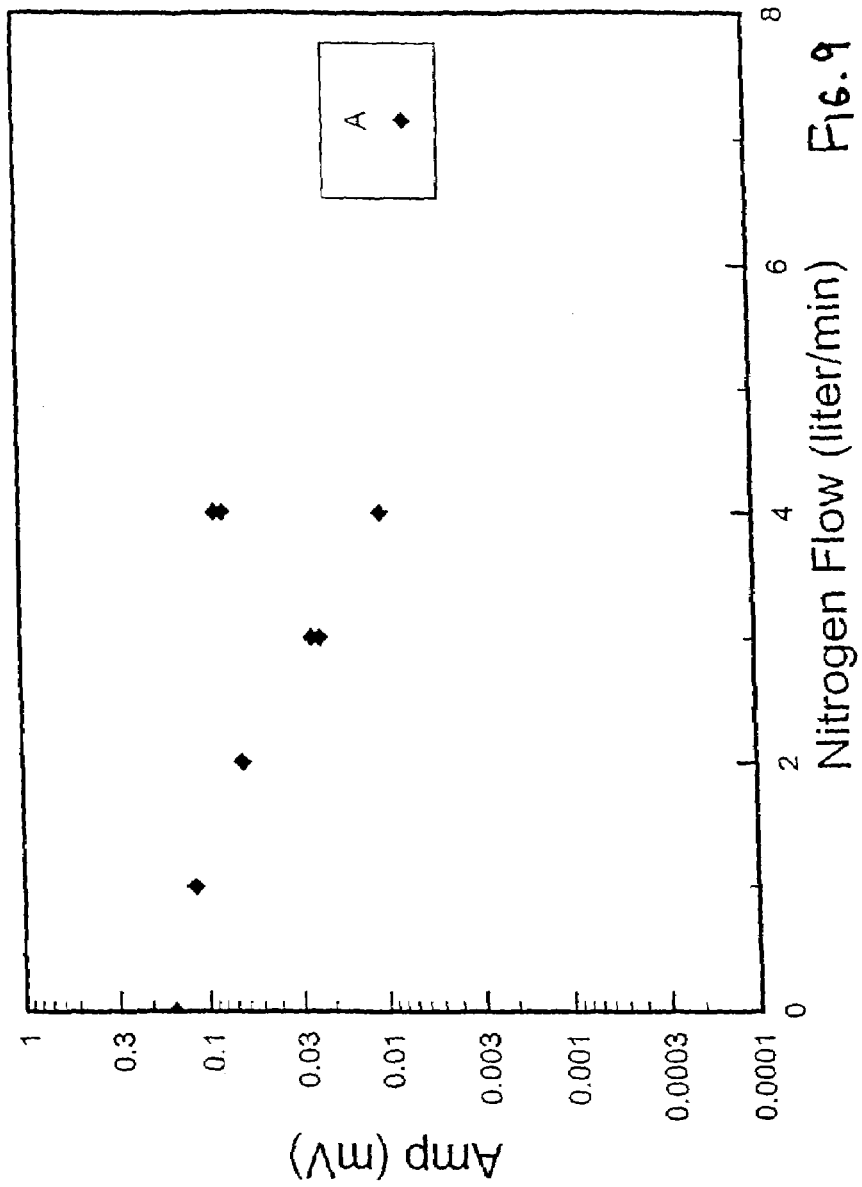
FIG. 9 is a graphic illustration of the change in amplitude of a transmitted ultrasonic signal in the autoclave reactor of the present invention as a function of nitrogen flow in Therminol at 20° C. and 600 rpm.

FIG. 9 illustrates the change in the amplitude of the transmitted ultrasonic signal in the reactor as a function of nitrogen flow in Therminol at 20° C. and 600 rpm. FIG. 9 also suggests that the amplitude is approximately an inverse exponential function of the nitrogen flow. The impedances of the two media will determine the transmission of the wave from one medium to another and the amount of reflection of sound at the boundary between the two media. The following equation expresses the value of the sound power transmission coefficient, $\alpha_t$, for transmission in terms of the acoustic impedance for media 1 and 2 respectively:

$$\alpha_t + (4Z_2 Z_1)/(Z_1 Z_2) \quad (2)$$

If the impedances of two media are widely separated, e.g., nitrogen and Therminol, then most of the energy is reflected back in the first medium (Therminol) with some transmission into the second medium (nitrogen). It can be assumed that the ultrasonic pulse cannot penetrate through much of the nitrogen/Therminol interface at the current experimental frequency due to the acoustic impedance mismatch of this combination. Therefore, the amount of attenuation of the ultrasound beam by nitrogen bubbles is proportional to the gas volume fraction, but also can be dependent on bubble size present in the path of the ultrasound wave, especially when the ultrasound wave is near the resonance frequency. The attenuation is greatest at frequencies near resonance. The frequency ($\omega_r$) at which resonance occurs depends on the physical properties of the component phases and the bubble size, and is expressed by the following:

$$\omega_r^2 = 3\rho_b c_b^2/(\rho r^2) \quad (3)$$

where $\rho$ is the density of the Therminol, $\rho_b$ and $c_b$ are the density and ultrasonic velocity of the nitrogen bubbles, respectively, and r is the radius of the nitrogen bubbles. In the arrangement disclosed herein, the frequency utilized was not near the bubble resonance frequency; therefore, the data collected was not affected by the resonance effect. The transmitted ultrasonic signal can be approximated by the exponential relationship:

$$A/A_0 = \exp[-f(d_b)\epsilon] \quad (4)$$

where $\epsilon$ is the void fraction and $f(d_b)$ is a function dependent on the Sauter mean diameter. This correlation shows that the $A/A_0$ ratio has an exponential relationship with both the void fraction and with a function dependent on the bubble diameter. The effect of air bubble diameter on $A/A_0$ ratio was found to be significant, with $A/A_0$ decreasing with increasing bubble size. The transmitted ultrasonic signal may also be expressed by an exponential relationship:

$$A/A_0 = \exp[\Gamma x/8S(kd_b/2)] = \exp[\Gamma x/8S(k3\epsilon/\Gamma)] \quad (5)$$

where $\Gamma$ is the volumetric interfacial area, x is the travel distance in the path, S is the scattering coefficient, k is the wave number of the ultrasonic waves which surrounds the bubble, $\epsilon$ is the gas holdup and $d_b$ is the Sauter mean bubble diameter. Equation (5) shows that the $A/A_0$ ratio has an exponential relationship with the interfacial area and the scattering cross section, which is a function of the bubble radius, gas holdup and the wave number of the ultrasonic wave surrounding the bubble. Decreasing $A/A_0$ as the nitrogen flow increased in FIG. 9 may be attributed to a combination of the void fraction, bubble size, the number of bubbles, and the scattering cross section. The results indicate that only the amplitude and not the transit time of the ultrasonic signal are affected by the nitrogen flow rate in the reactor under the current experimental conditions.

The influence of nitrogen flow and temperature on transit times and amplitude in Therminol at 600 rpm and 20, 100, 150, 200, 210, 220, 225, 230, 240, 250, and 260° C. were studied. The transit time and amplitude ratio were measured at nitrogen flows of 0, 1, 2, 2.5, 3, 4 liter/min in Therminol at 600 rpm. At 2.5 liter/min, a different stirring speed of 900 rpm was also utilized. The typical results obtained at 250° C. are shown in FIGS. 10 and 11.

Figure 10:
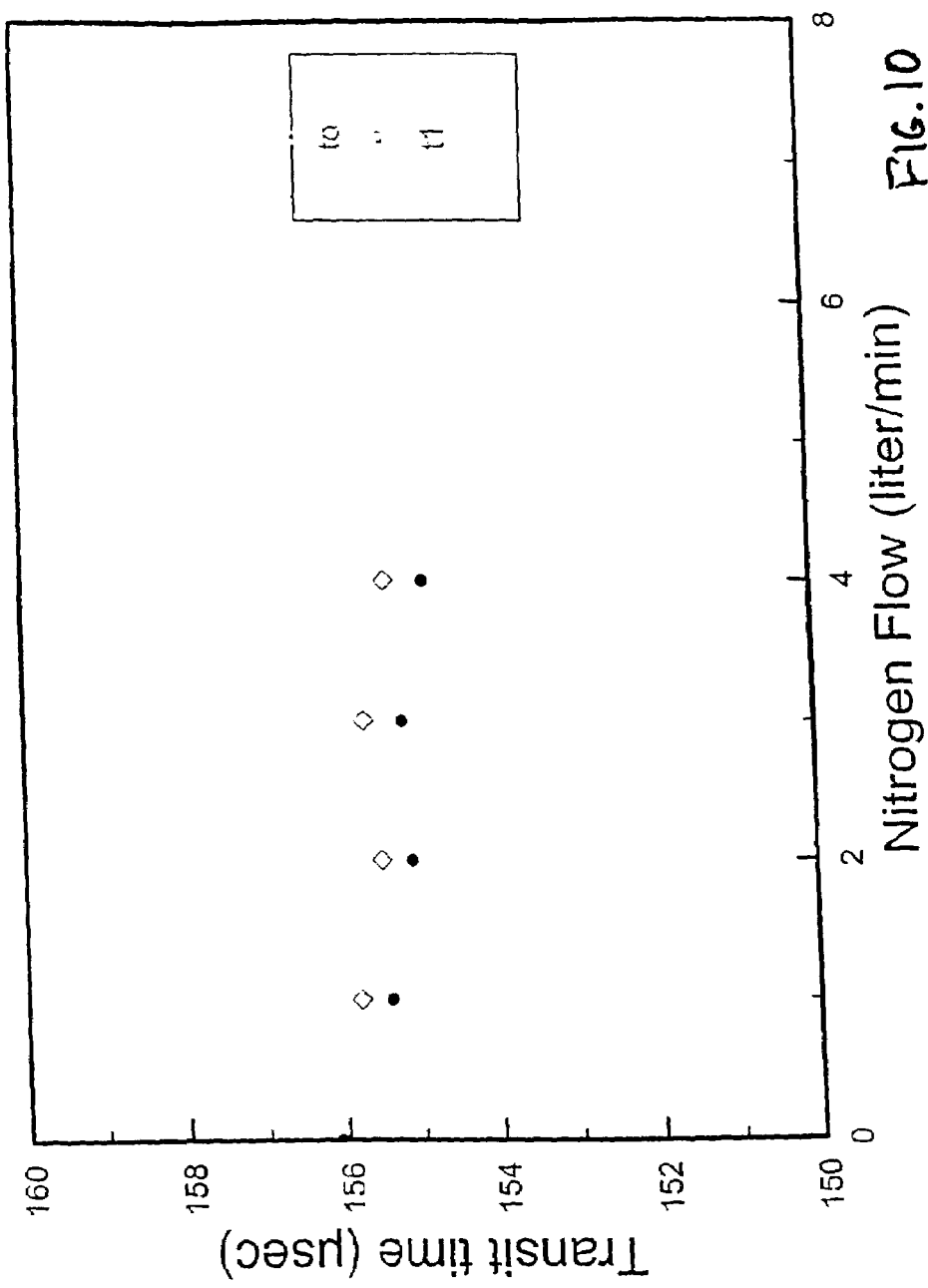
FIG. 10 is a graphic illustration of the effect of nitrogen flow on acoustic wave transit time, $t_0$.

FIG. 10 shows the effect of the nitrogen flow on the transit time, $t_o$. It is approximately 156.1 μs at no nitrogen flow in Therminol at 600 rpm and 250° C. The transit time $t_o$ is approximately 155.2 μs at all nitrogen flows. Apparently the transit time is unaffected by the nitrogen flow under the current experimental conditions (nitrogen varied from 1 to 4 liter/min); because what we measured was the signal not transmitted through the nitrogen. The measured transit time; therefore, should not be affected by the nitrogen flow. However, the slight difference in transit time with and without the presence of nitrogen flow still needs further investigation. Again, the speed of sound travel through the Therminol can be determined by using $t_o$ and equation (1). The speed of sound in Therminol at 250° C. is 783 m/sec (based on the $t_o$ of 155.2 μs).

Figure 11:
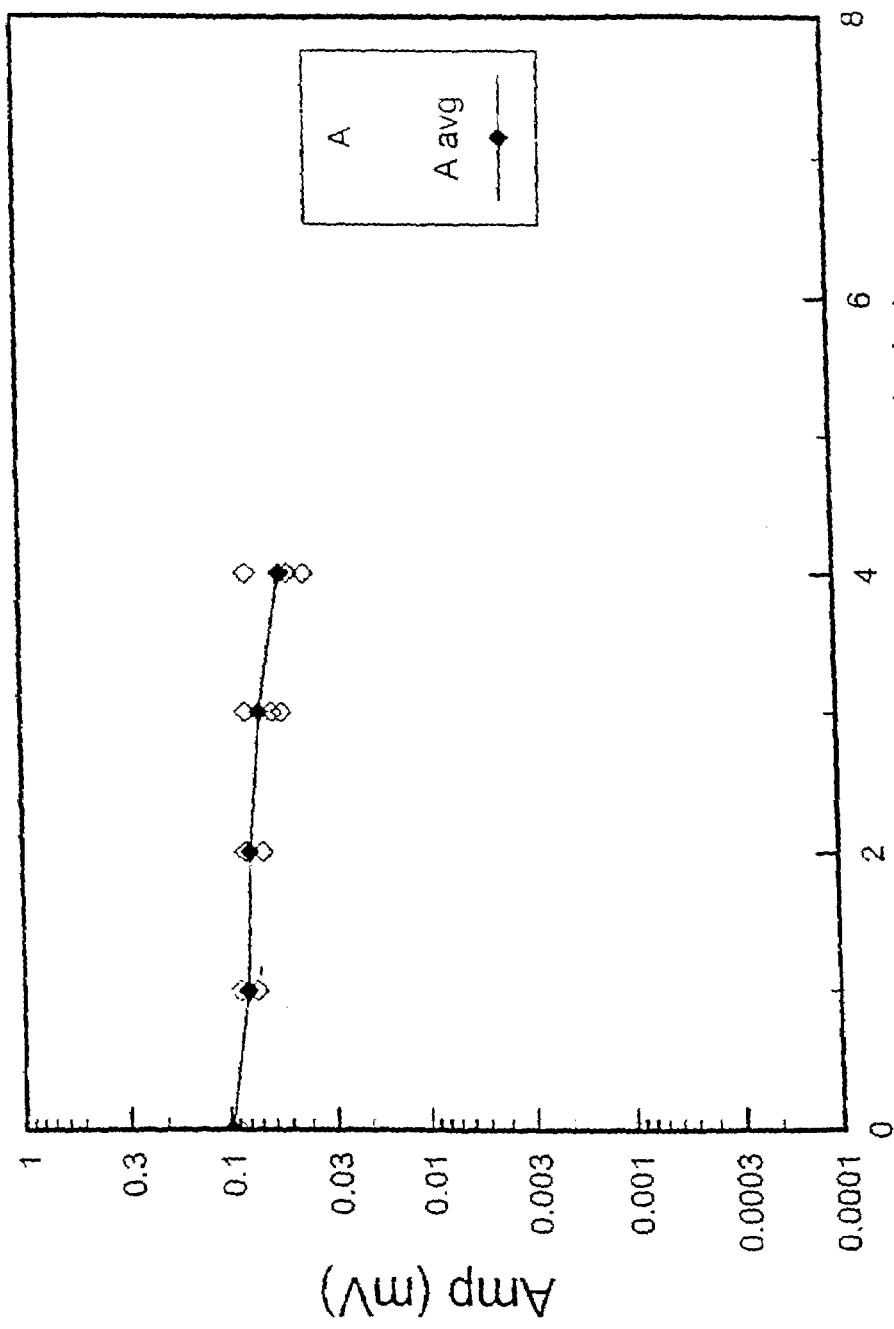
FIG. 11 graphically illustrates the change in amplitude of a transmitted ultrasonic signal in the autoclave reactor of the present invention as a function of nitrogen flow in Therminol at 250° C. and 600 rpm.
Figure 12:
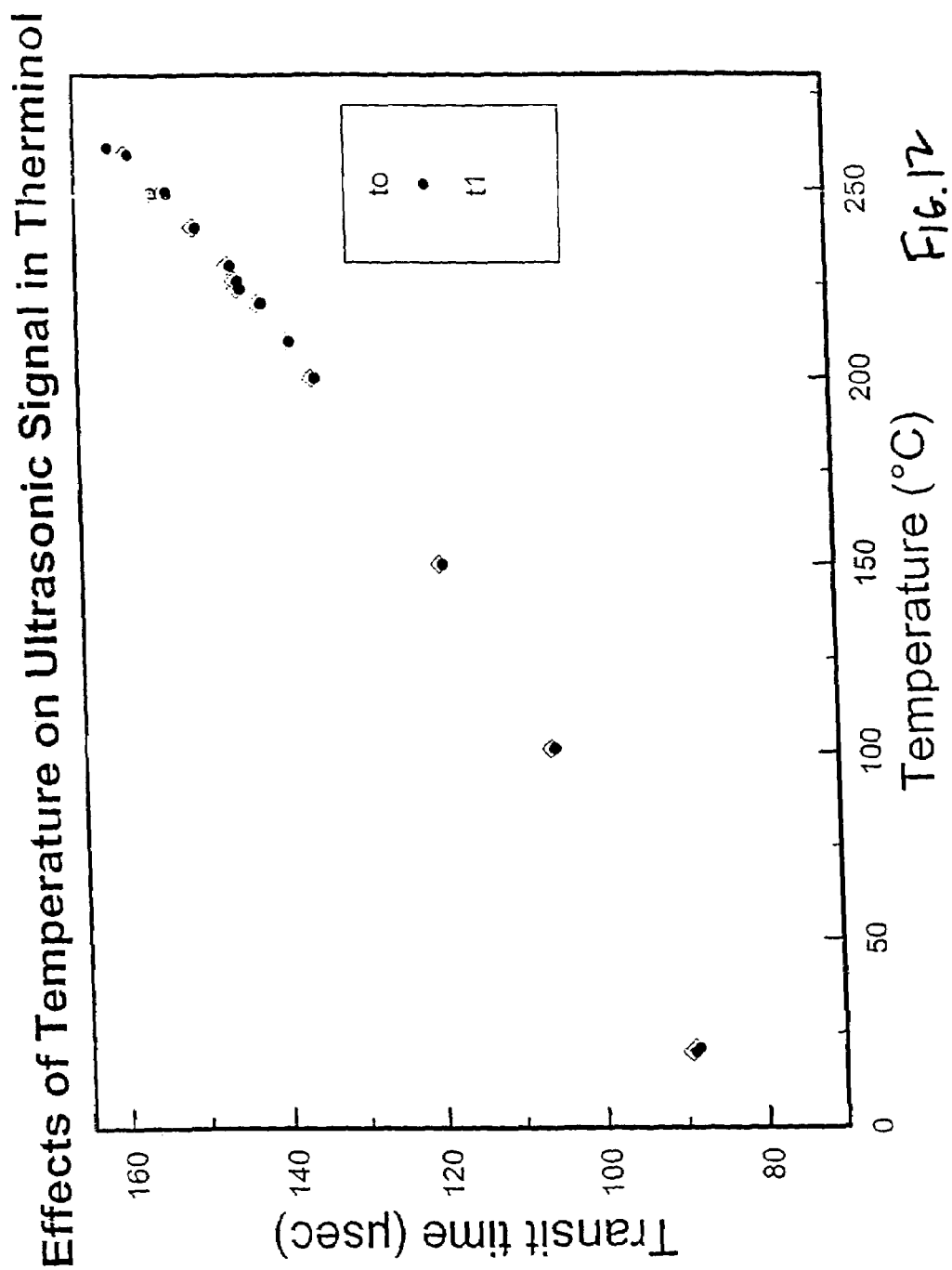
FIG. 12 graphically illustrates the effect of temperature on ultrasonic measurement in Therminol under the conditions indicated.

FIG. 11 illustrates the change in the amplitude of the transmitted ultrasonic signal in the reactor as a function of nitrogen flow in Therminol at 250° C. and 600 rpm. FIG. 11 also suggests that the average amplitude approximately fits into an inverse exponential function of the nitrogen flow as shown in FIG. 9. However, the slope obtained under 250° C. is not as steep as that in FIG. 9 obtained under ambient condition.

The temperature of the Therminol greatly affects the ultrasonic signal. The effect of temperature on ultrasonic measurement in Therminol under conditions of constant stirring speed of 600 rpm and gas flow of 2 liter/min in the autoclave reactor is presented in FIG. 12. These results show that the measured transit time is significantly influenced by the temperature of Therminol. The transit time is around 88 μs at 20° C. It then increases to approximately 160 μs as the temperature reaches 260° C. The increase in transit time as the temperature increases is probably due to the change in density, viscosity and other physical properties in the Therminol which result in the variation of the ultrasonic signal with temperatures.

Figure 13:
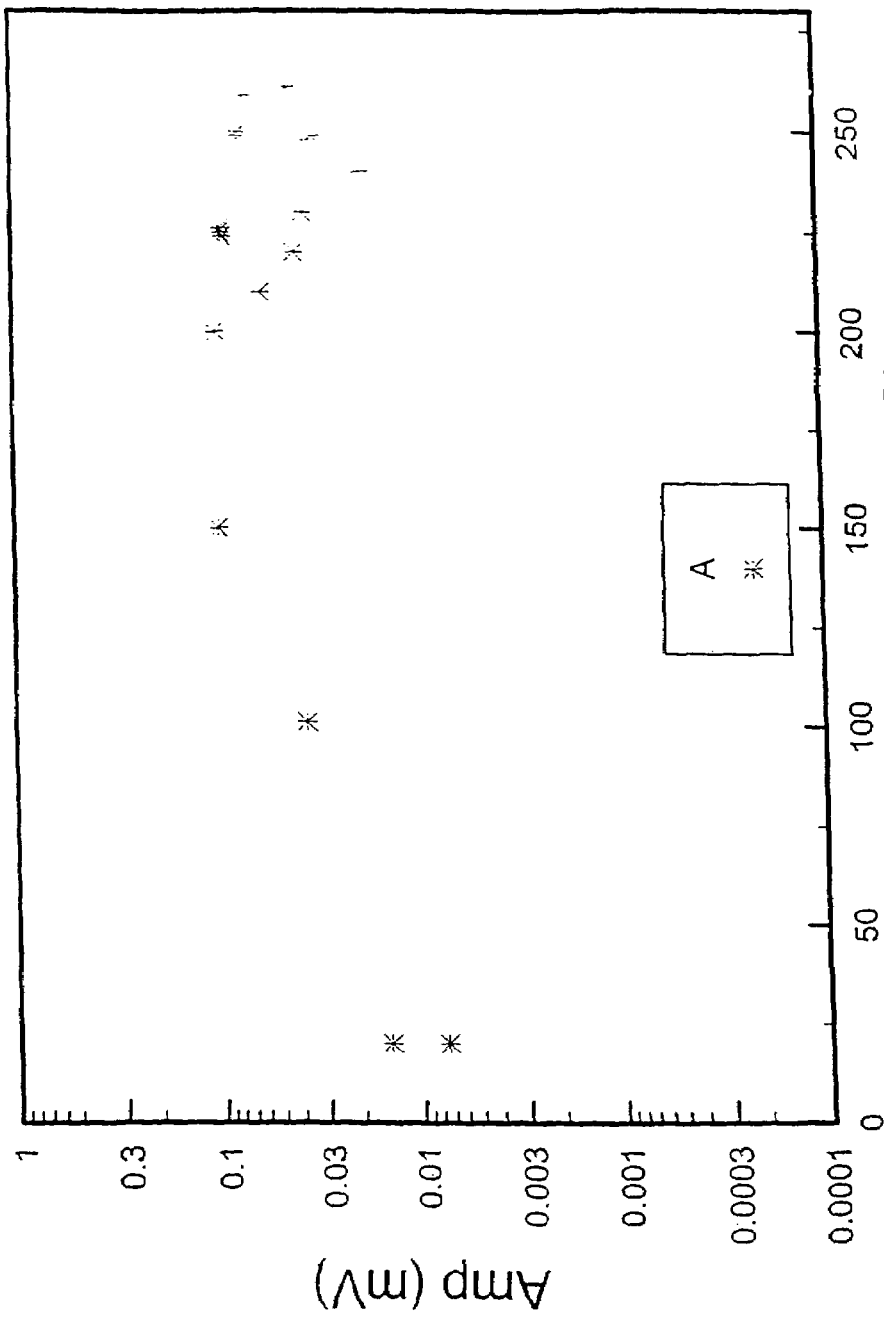
FIG. 13 graphically illustrates the effects of temperature on the amplitude of an ultrasonic signal in Therminol under the indicated conditions.

The effects of temperature on the amplitude of the ultrasonic signal in Therminol under the conditions of a constant stirring speed of 600 rpm and gas flow of 2 liter/min are illustrated in FIG. 13. Unlike the transit time shown in FIG. 12, there is no clear correlation between the amplitude and the temperature of Therminol.

Figure 14:
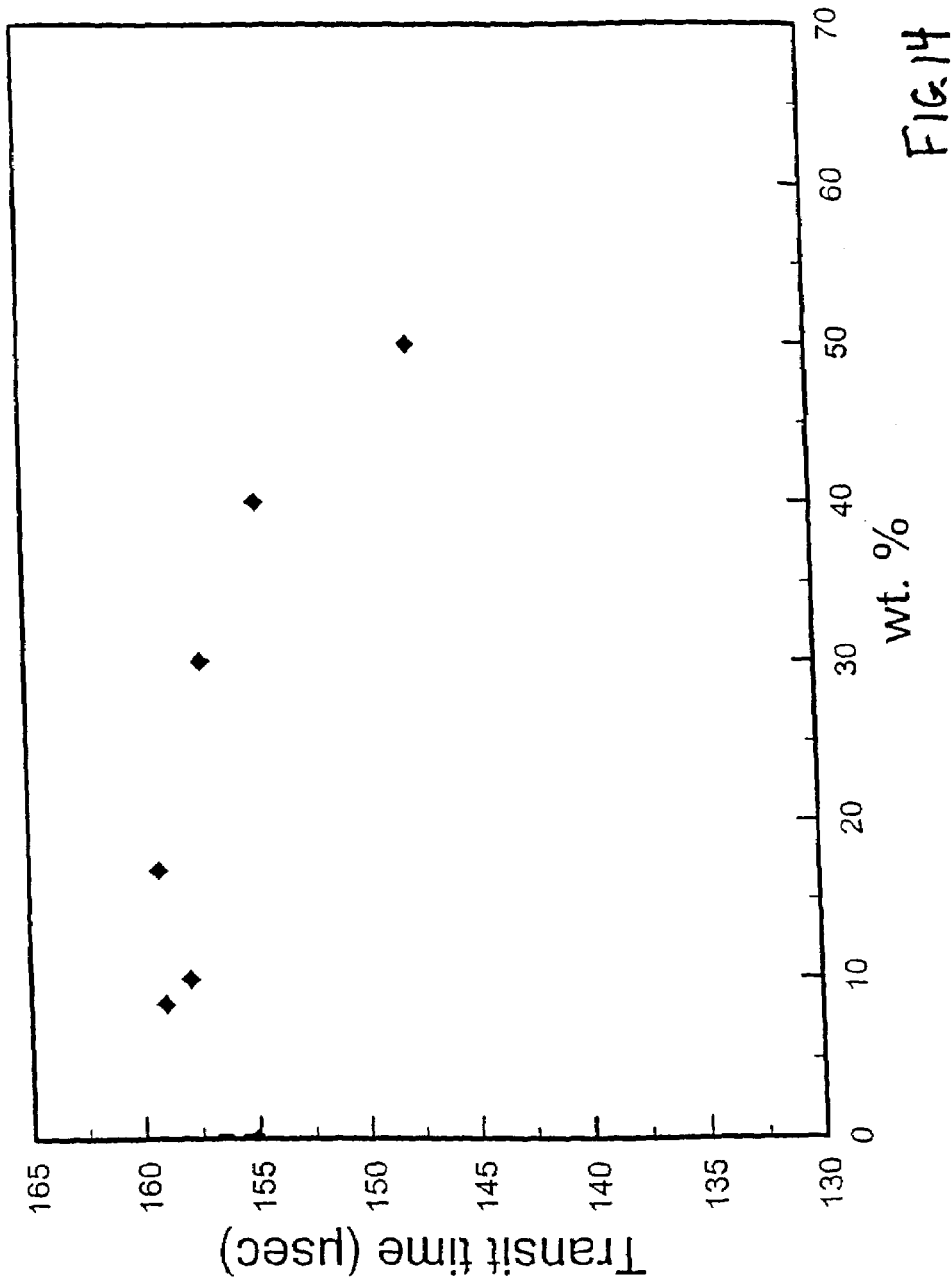
FIG. 14 graphically illustrates the effect of silicon metal on transit time ($t_4$) of a transmitted ultrasonic signal in the autoclave reactor of the present invention under the indicated conditions.

FIG. 14 presents the effect of silicon metal (wt. %, solid/liquid) on transit time ($t_4$) of the transmitted ultrasonic signal in the reactor at a constant temperature of 250° C., a constant stirring speed (800 or 900 rpm) and with a nitrogen flow of 2.5 liter/min. The transit time is approximately 155.5 to 156.5 μs in the absence of any silicon metal in the reactor. With the introduction of 8.43 wt. % of silicon metal, the transit time increases to 157.9 µs. Subsequently increasing the concentration of silicon metal to 16.86 wt. % leads to an increase of transit time to 159.2 µs. Further, increasing the concentration of silicon metal to 30 wt. % results in decreasing of the transit time to 157.2 µs. A further decrease in transit time shows the solids concentration increases in the reactor to 40 and 50 wt. %. Transit time was approximately 154.6 µs with 40 wt. % of solids, but decreased to approximately 147.7 µs as the solids concentration increased to 50 wt. %.

Figure 15:
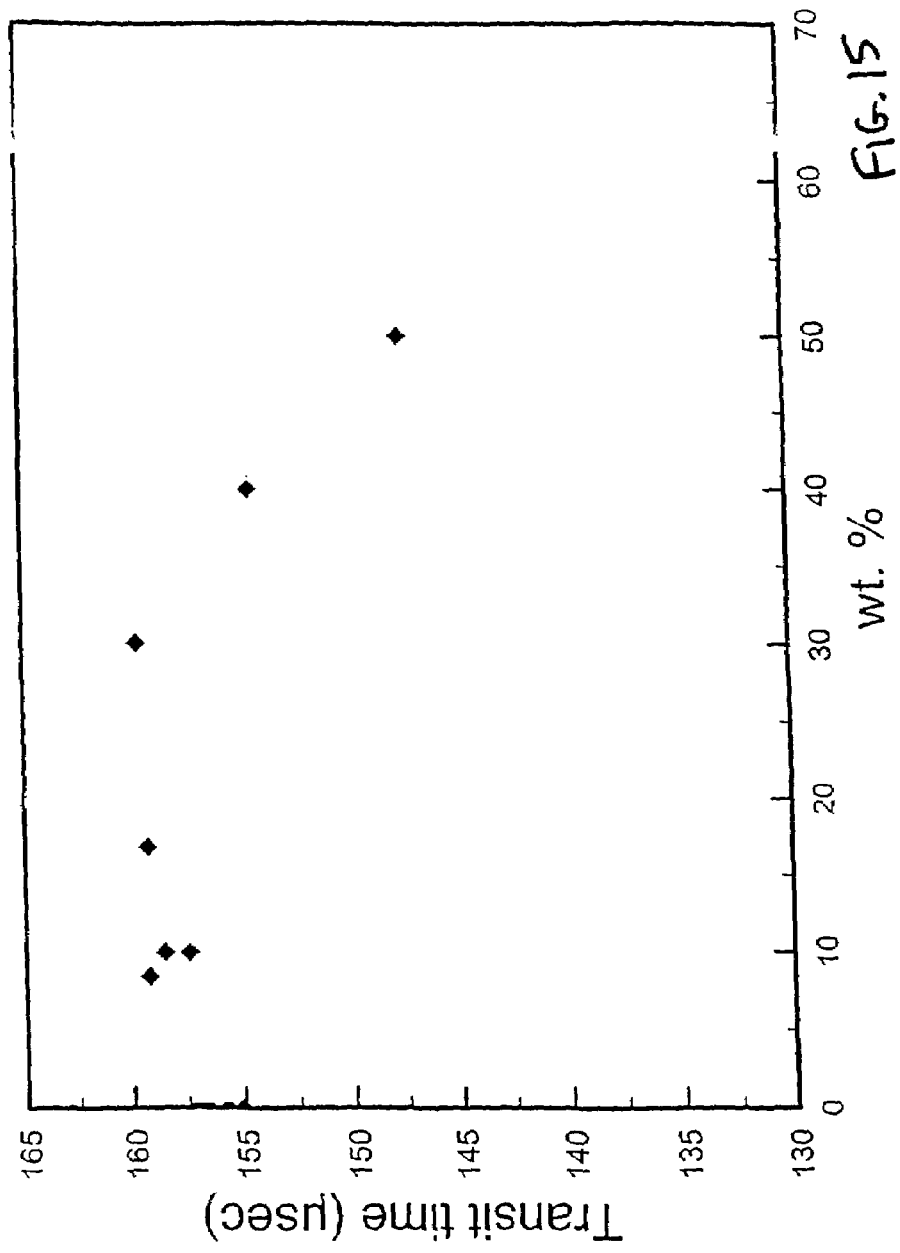
FIG. 15 graphically illustrates the effect of silicon metal on transit time ($t_4$) of a transmitted ultrasonic signal in the autoclave reactor under the same conditions as shown in FIG. 14, except for a stirring speed of 600 rpm.

FIG. 15 illustrates the effect of silicon metal on transit time ($t_4$) of the transmitted ultrasonic signal in the reactor under the same experimental conditions as shown in FIG. 14, except the stirring speed utilized is 600 rpm instead of 800/900 rpm. Trends similar to those observed in FIG. 14 are also found in FIG. 15. The transit time is approximately 155.8 to 157.2 µs in the absence of any silicon metal in the reactor. The introduction of 8.43 wt. % of silicon metal, increases the transit time to 159.2 µis. Subsequently, increasing the concentration of silicon metal to 16.86 wt. % leads to an increase of transit time to 159.2 µis. Increasing the concentration of silicon metal to 30 wt. % results in the transit time reaching 159.6 µis. Then a decrease in transit time is observed as the solids concentration is increased in the reactor to 40 and 50 wt. %. It is approximately 154.5 µs with 40 wt. % of solids, but decreases to approximately 147.6 µs as the solids concentration reaches to 50 wt. %.

Figure 16:
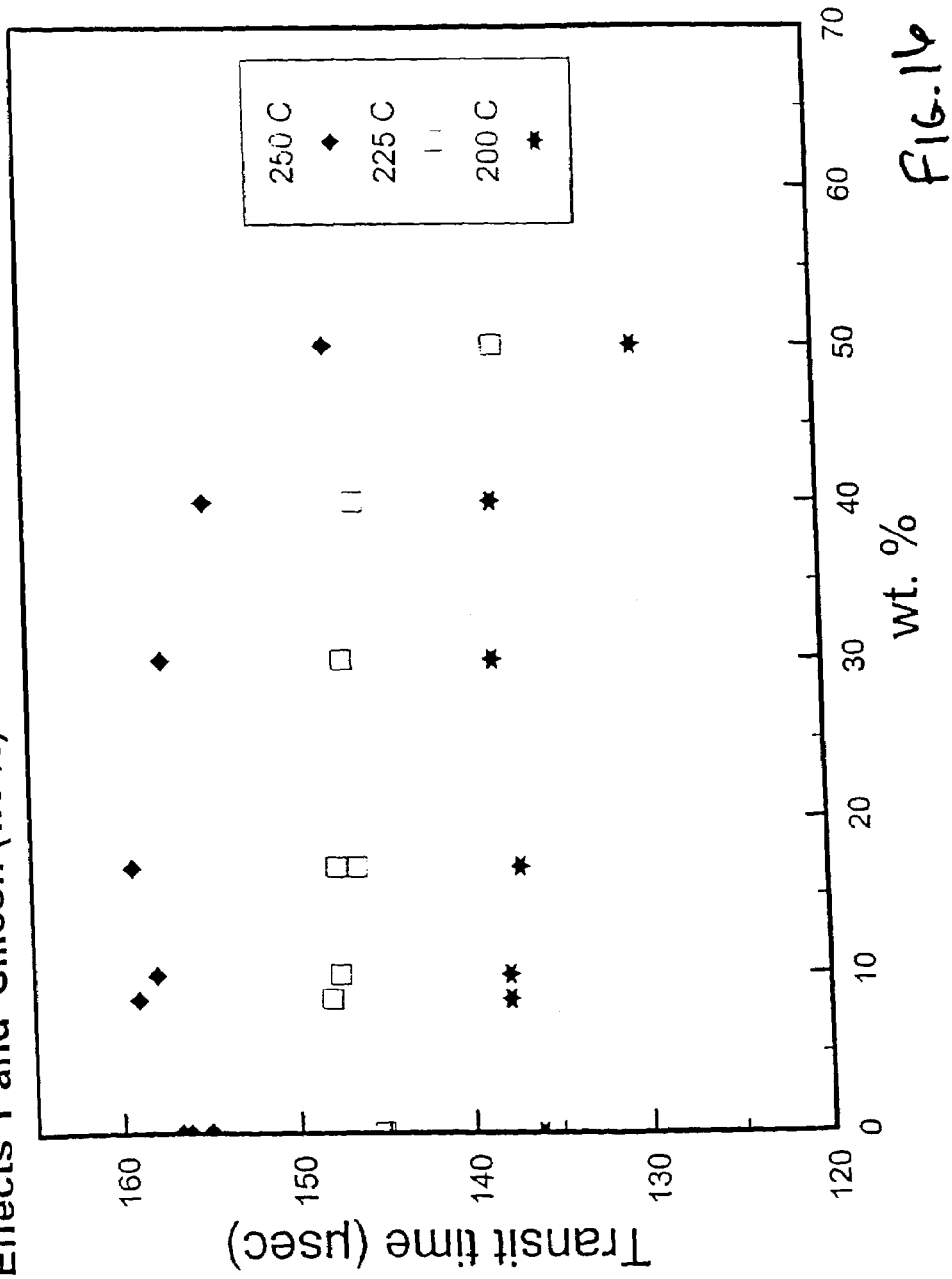
FIG. 16 shows the effect of silicon metal on transit time ($t_4$) of a transmitted ultrasonic signal in the autoclave reactor under the indicated conditions.
Figure 17:
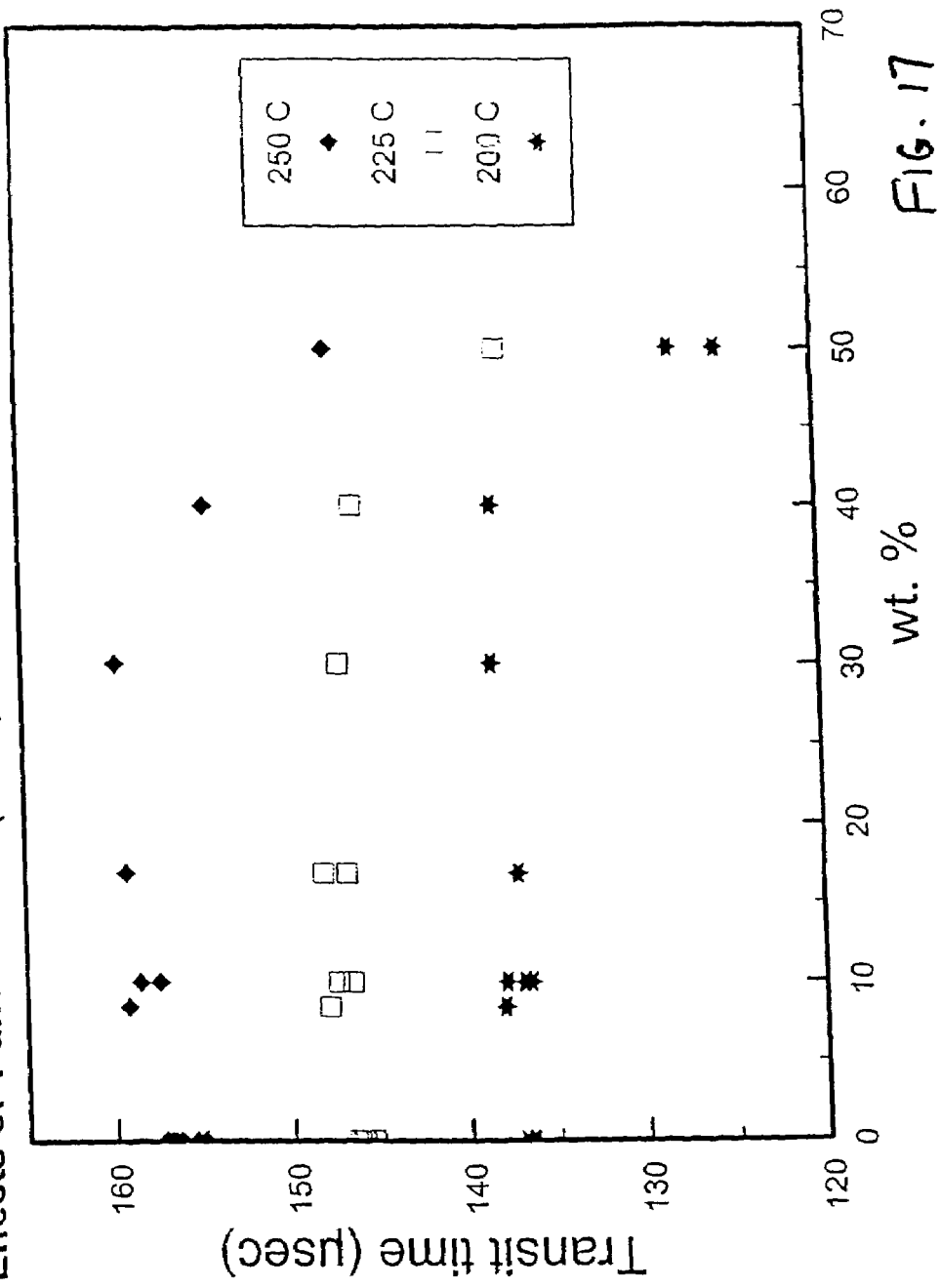
FIG. 17 graphically illustrates the effect of silicon metal on transit time of a transmitted ultrasonic signal under conditions similar to those in FIG. 16, except for a stirring speed of 600 rpm.

FIG. 16 shows the effect of silicon metal (wt. %, solid/liquid) on transit time ($t_4$) of the transmitted ultrasonic signal in the reactor at temperatures of 200, 225 and 250° C., respectively, with a constant stirring speed (800 or 900 rpm) and with a nitrogen flow of 2.5 liter/min. Similar trends observed in FIG. 14 for 250° C. are also found at the lower temperatures of 200 and 225° C. At any given constant temperature, increasing the concentration of silicon metal up to 30 or 40 wt. %, leads to an increase of the transit time ($t_4$). However, further increases in the concentration of silicon metal leads to a decrease of the transit time. Similar results are also observed under the same experimental conditions but with a stirring speed of 600 rpm as illustrated in FIG. 17. The major difference among the trends displayed in FIGS. 14, 15 and 16 is the range of concentration when the transit time starts to decrease. The range for 250° C. is between 20 and 30 wt. %. For the case of 225° C., the range is between 30 and 40 wt. %. At the lower temperature of 200° C., the range is between 40 and 50 wt. %. This seemingly temperature dependence on the range of concentration when the transit time starts to decrease is probably due to the evaporation of Therminol. The evaporation of the Therminol was noticeable during the experiments. To overcome this complication which would affect the true wt. % calculation, a condenser was installed on the top of the reactor for the last evaluation of the invention. Most of the data presented herein was collected without the condenser located on the top of the reactor.

Figure 18:
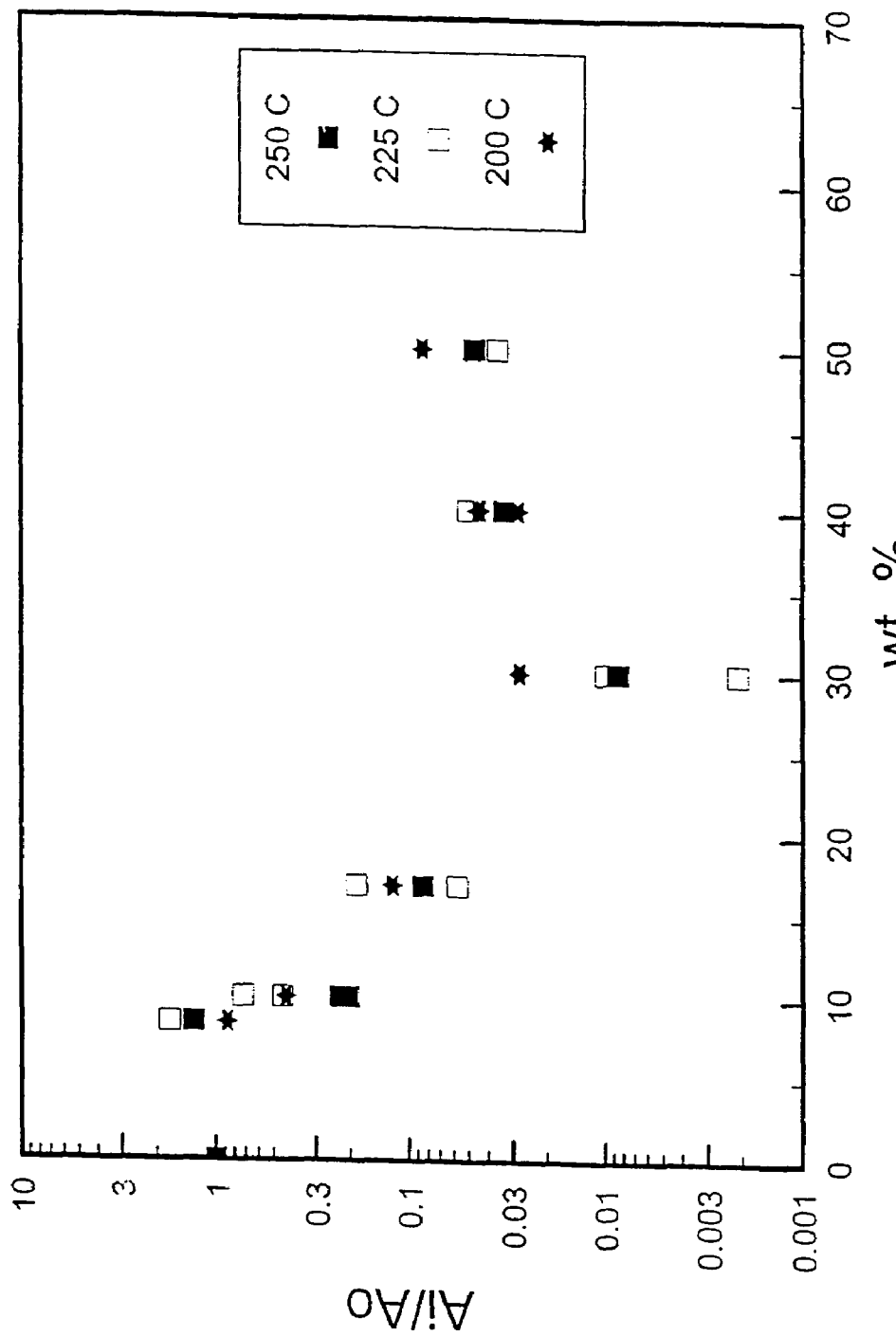
FIG. 18 graphically illustrates the effect of silicon metal (wt. %, solid/liquid) on the amplitude ratio of a transmitted ultrasonic signal $A_i/A_o$ with and without ($A_i$ with, $A_o$ without) the presence of silicon metal at the indicated temperatures.

FIG. 18 shows the effect of silicon metal (wt. %, solid/liquid) on the amplitude ratio of the transmitted ultrasonic signal $A_i/A_o$ ($A_i$ and $A_o$ are respectively the amplitude of the transmitted signals with and without the presence of silicon metal) at the temperature of interest. Experimental conditions in the reactor were temperatures of 250, 225, or 200° C., a constant stirring speed (600 rpm), and a nitrogen flow 2.5 liter/min. As illustrated in FIG. 18, the $A_i/A_o$ ratio decreased as the concentration of silicon metals increased from 0 to 30 wt. %. However, when the concentration was increased beyond 30 wt. %, $A_i/A_o$ increased as the concentration of silicon metal increased. This trend seems to correspond with the trends of transit time in FIGS. 16 and 17.

Figure 19:
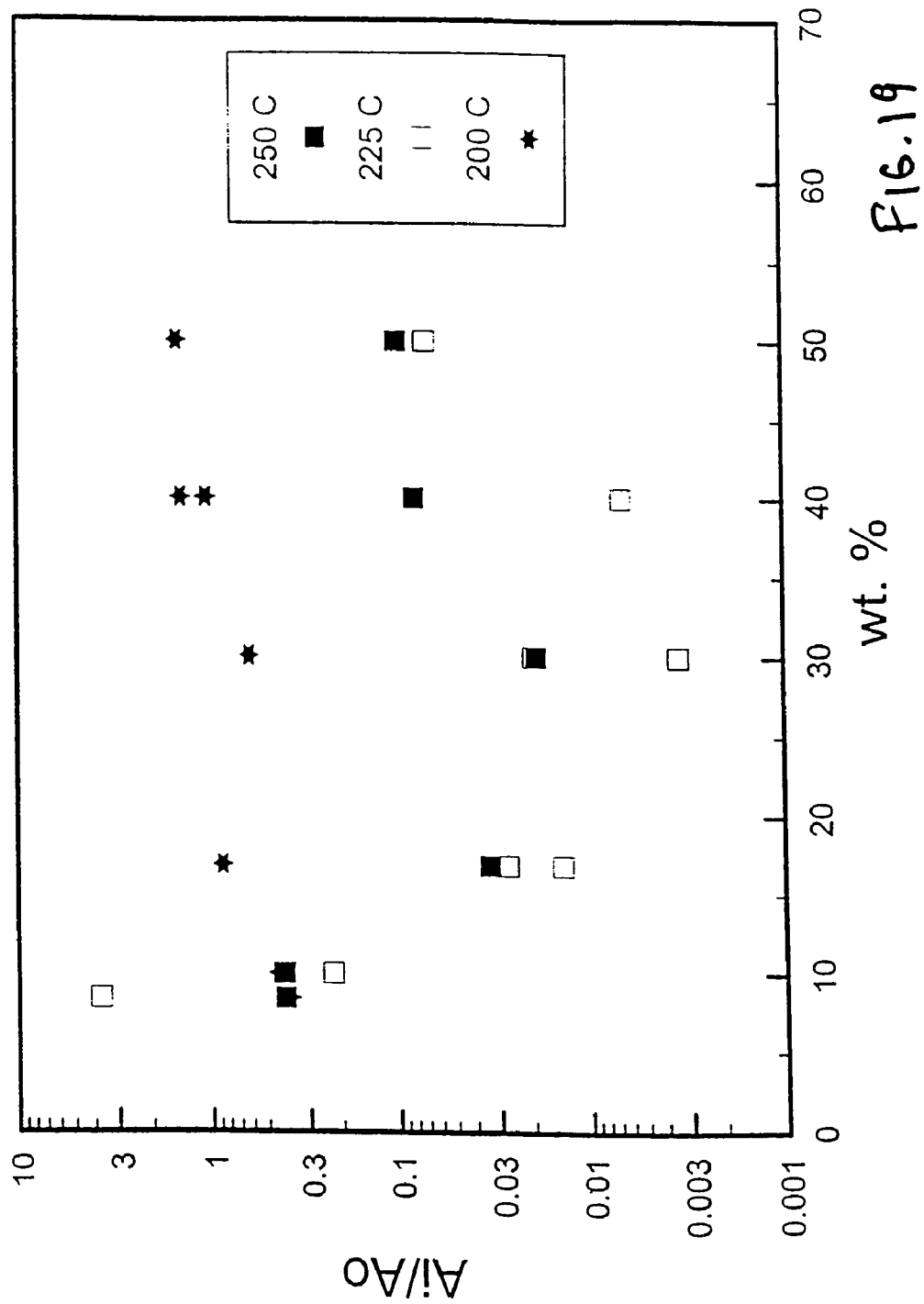
FIG. 19 graphically illustrates the effect of silicon metal on the amplitude ratio of a transmitted ultrasonic signal $A_i/A_o$ under the same conditions as shown in FIG. 18, except the stirring speed was changed to 800/900 rpm from 600 rpm.

FIG. 19 illustrates the effect of silicon metal on the amplitude ratio of the transmitted ultrasonic signal Ai/Ao under the same experimental conditions as shown in FIG. 18, except the stirring speed utilized was 800/900 rpm instead of 600 rpm. Similar trends as observed in FIG. 18 can also be found in FIG. 19, although the data were more scattered in FIG. 19 than in FIG. 18. In general, the $Ai/A_o$ ratio decreased as the concentration of silicon metals increased from 0 to 30 wt. %. However, when the concentration was increased beyond 30 wt. %, the $A_i/A_o$, increased as the concentration of silicon metal increased. This trend seems to correspond with the trends of transit time in FIGS. 16 and 17. The attenuation in the inertial regime has been shown to scale with $(\mu w)^{1/2}/a$. This clearly indicates that the attenuation changes when the dominate regime changes. The Re values at 250° C. suggest the present invention is in the transition regime between the inertial and viscous regime. Together with the changes in the trends of $A_i/A_o$, transit time, and ka, the data suggest a change in the dominate regime from inertial to viscous under conditions as described herein.

Figure 20:
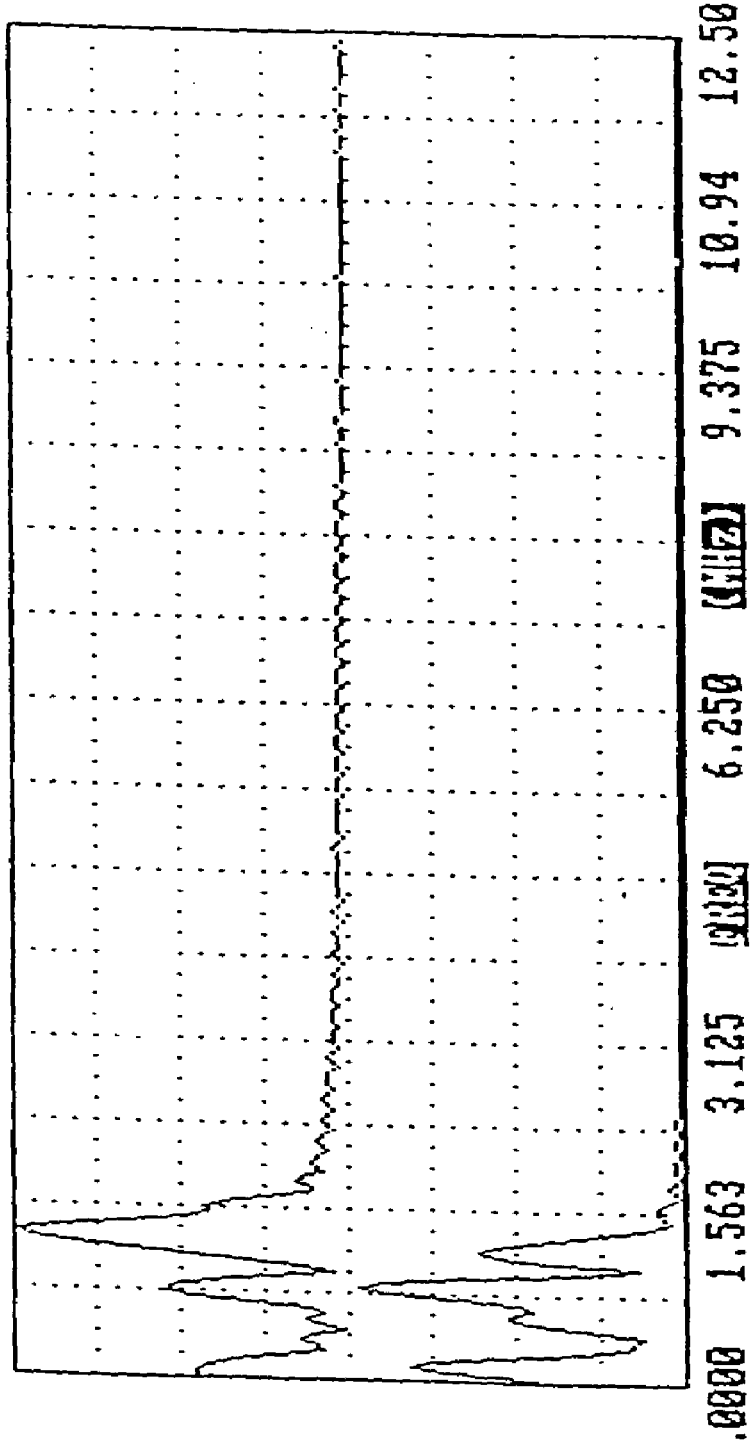
FIG. 20 illustrates graphically the effect of particle sizes on the ultrasonic spectrum of a constant solid concentration, 30 wt. %, with a constant nitrogen flow of 2.5 liter/min, 800 rpm, and temperature 250° C. within the autoclave reactor, where the lower curve was obtained with a wider range silicon metal.

Moreover, the effects of particle sizes on the ultrasonic spectrum can be clearly seen by comparing the collected spectrum at the same solids concentration but with different particle sizes. FIG. 20 demonstrates the effects of particle sizes on the ultrasonic spectrum at a constant solid concentration, 30 wt. %, with a constant nitrogen flow of 2.5 liter/min, 800 rpm, and temperature of 250° C., in the stirred reactor. The upper graph in FIG. 20 is the normalized spectrum collected with a narrower range silicon metal (17780-33-1). The lower graph in FIG. 20 is obtained with a wider range silicon metal (17780-33-2). The particle size greatly affects the peak frequency. Three distinguishable peaks can be identified in FIG. 20. The peak centers are 0.11, 0.83, and 1.36 MHz. Four distinguishable peaks can be identified from FIG. 20. The peaks centers are 0.14, 0.63, 0.86 and 1.24 MHz. These changes are significant and may be used to correlate the sizes of silicon metal at a given solids concentration.

Figure 21:
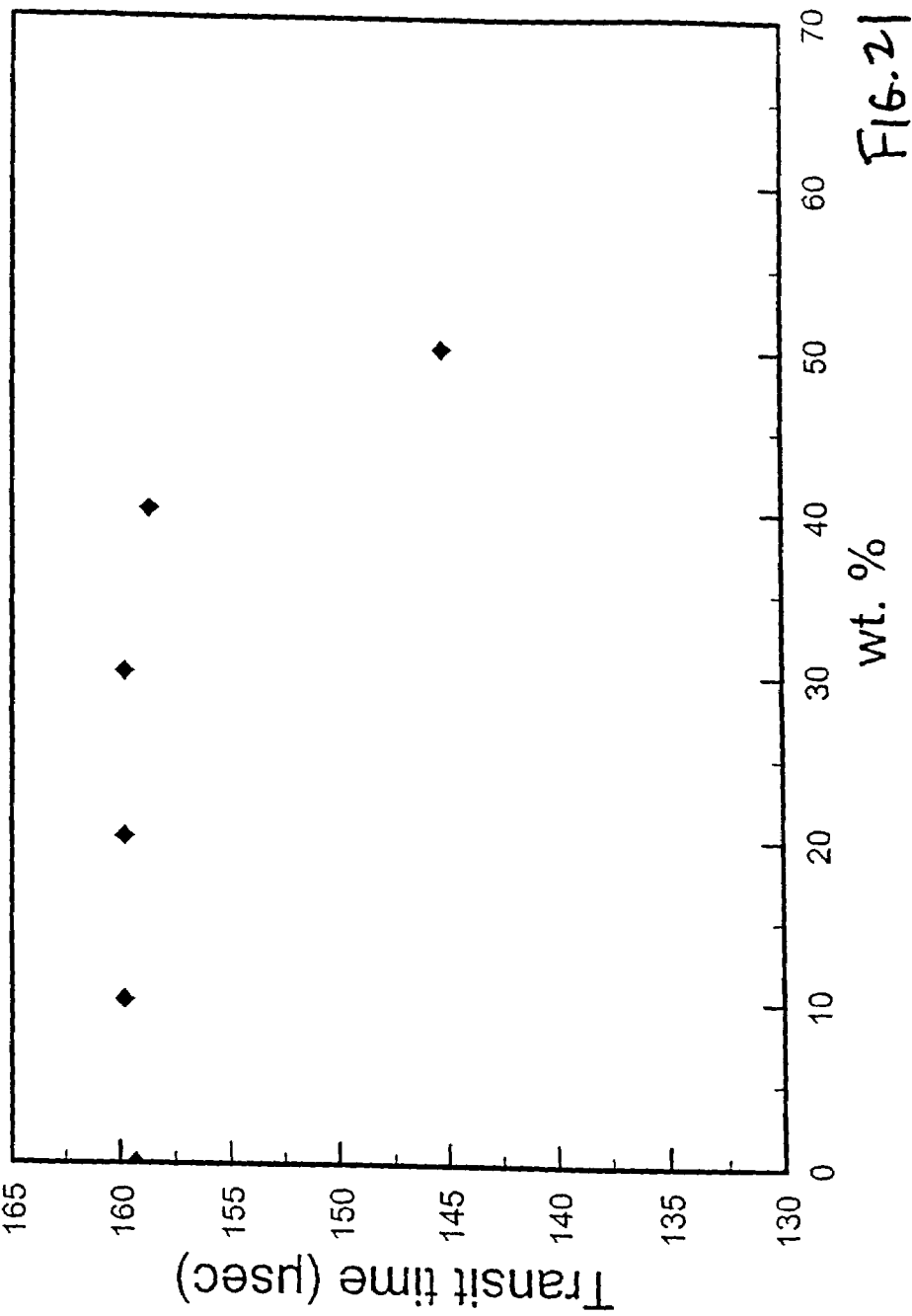
FIG. 21 graphically illustrates the effect of silicon metal (wt. %, solid/liquid) on transit time ($t_4$) of a transmitted ultrasonic signal in the autoclave reactor at a constant temperature of 250° C., a constant stirring speed of 800 rpm, and a nitrogen flow of 2.5 liter/min.

FIG. 21 presents the effect of silicon metal (wt. %, solid/liquid) on transit time ($t_4$) of the transmitted ultrasonic signal in the reactor at a constant temperature of 250° C., a constant stirring speed (800 rpm) and with a nitrogen flow of 2.5 liter/min. The transit time was approximately 159.3 µs in the absence of any silicon metal in the reactor. The introduction of 10 wt. % of silicon metal increased the transit time to 159.8 µs. Subsequently, increasing the concentration of silicon metal to 20 and 30 wt. % led to no further change of the transit time from 159.8 µs. Increasing the concentration of silicon metal to 40 wt. % (volume ratio of 0.22) resulted in the transit time decreasing to 158.7 µs. A further decrease in transit time was observed as the solids concentration increased to 50 wt. %. It was approximately 145.4 µs as the solids concentration reached 50 wt. %. It should be noted that this procedure was conducted when the condenser was installed on the top of the reactor.

Figure 22:
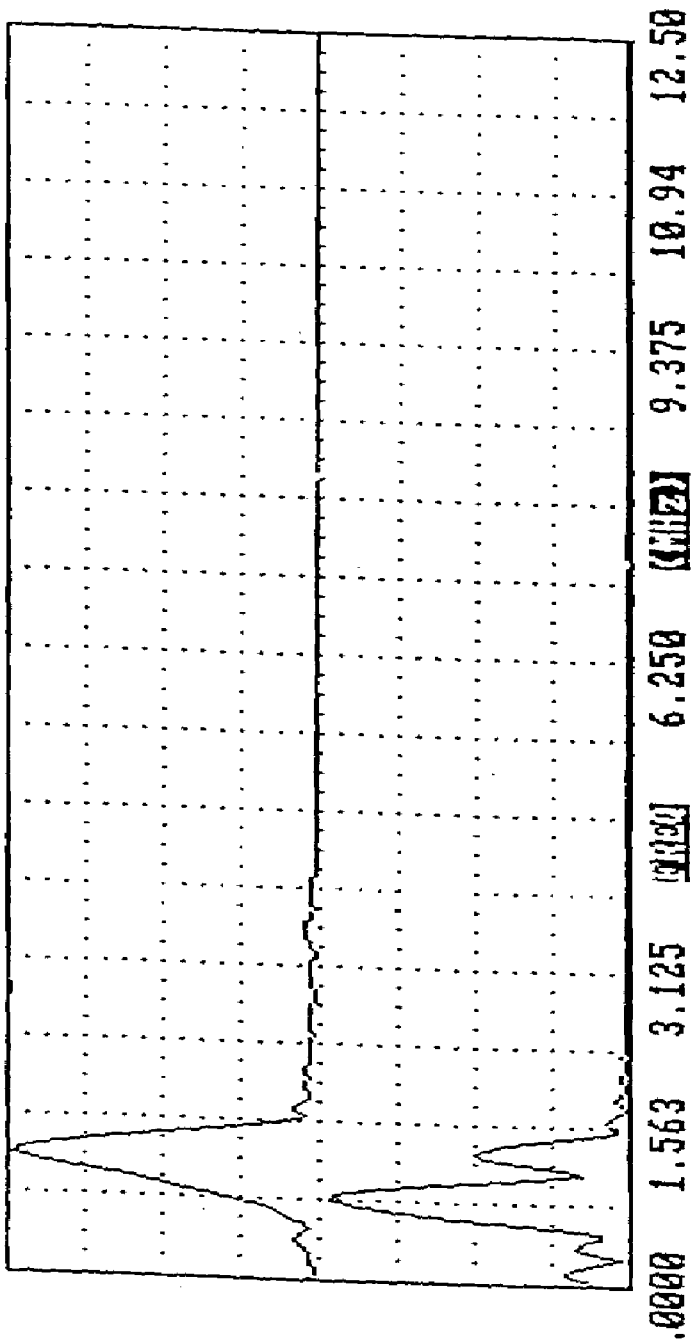
FIG. 22 is a graphic illustration of ultrasonic spectra under the same conditions as for FIG. 21 showing the effects of concentration of silicon metal on the ultrasonic spectrum at a constant nitrogen flow of 2.5 liter/min, 800 rpm and a temperature of 250° C. in the stirred autoclave reactor, where the upper curve is the normalized spectrum collected in the absence of silicon metal and the lower curve is for narrower range of silicon metal.
Figure 23:
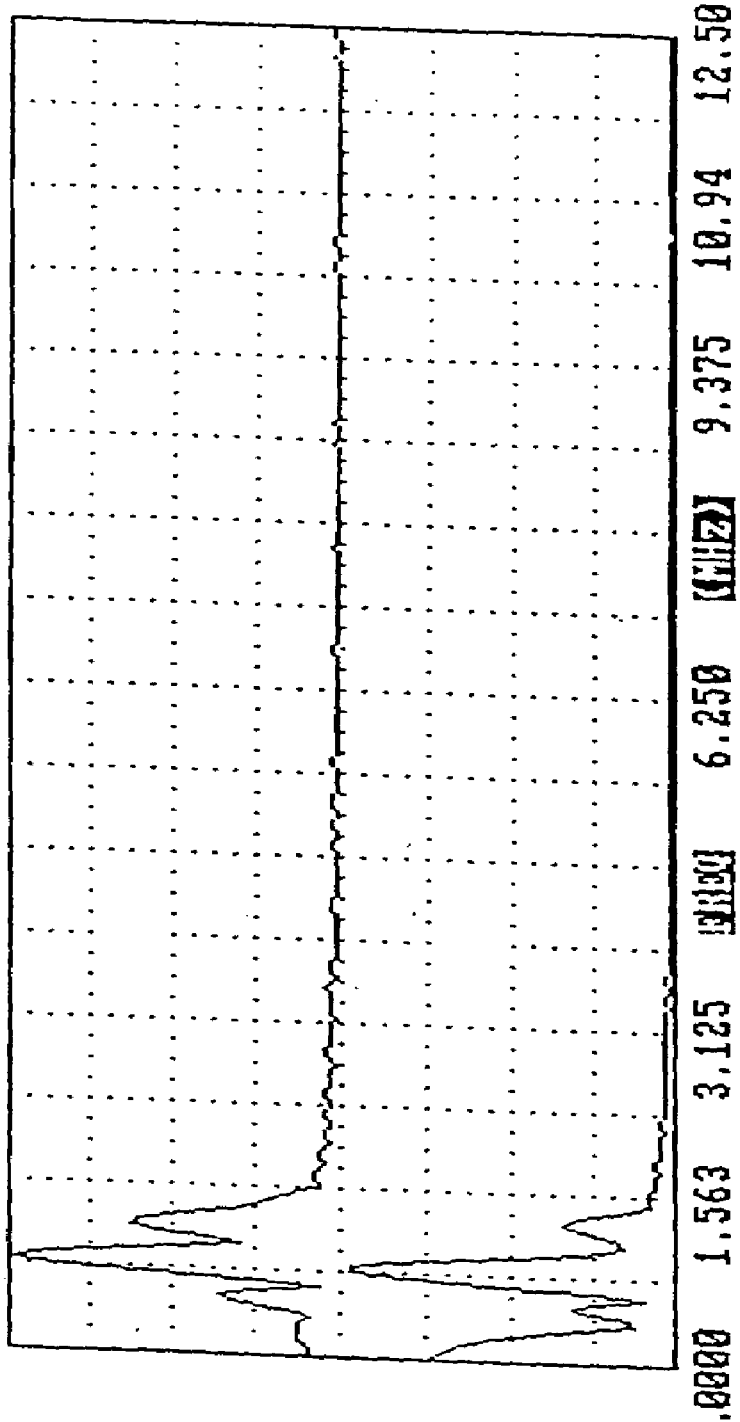
FIG. 23 graphically illustrates the normalized spectrum collected with a narrower range silicon metal at 40 (upper curve) and 50 (lower curve) wt. %.

Selected ultrasonic spectrums under the same experimental conditions as shown in FIG. 21 are illustrated in FIGS. 22 and 23. FIG. 22 shows the effects of concentrations of silicon metal (17780-33-1) on the ultrasonic spectrum at a constant nitrogen flow of 2.5 liter/min, 800 rpm and temperature of 250° C., in the stirred reactor. The upper graph in FIG. 22 is the normalized spectrum collected in the absence of silicon metal. The lower graph in FIG. 22 is the normalized spectrum collected with a narrower range silicon metal (17780-33-1) at 10 wt. %. The upper and lower graphs of FIG. 23 are respectively the normalized spectrum collected with a narrower range silicon metal (17780-33-1) at 40 and 50 wt. %. Significant differences in the peaks can be seen in FIGS. 22 and 23. These changes may be used to correlate the sizes of silicon metal at a given solids concentration. The ultrasound spectrum may provide other useful information in addition to the transit time and $A_i/A_o$. Our data of transit time and $A_i/A_o$ as a function of silicon metal concentration sometimes showed a range of ambiguity associated with having two concentrations that can result in the same transit time and $A_i/A_o$. However, using additional information such as the ultrasound spectrums as a function of silicon metal concentration, the ambiguity can be resolved.

Figure 24:
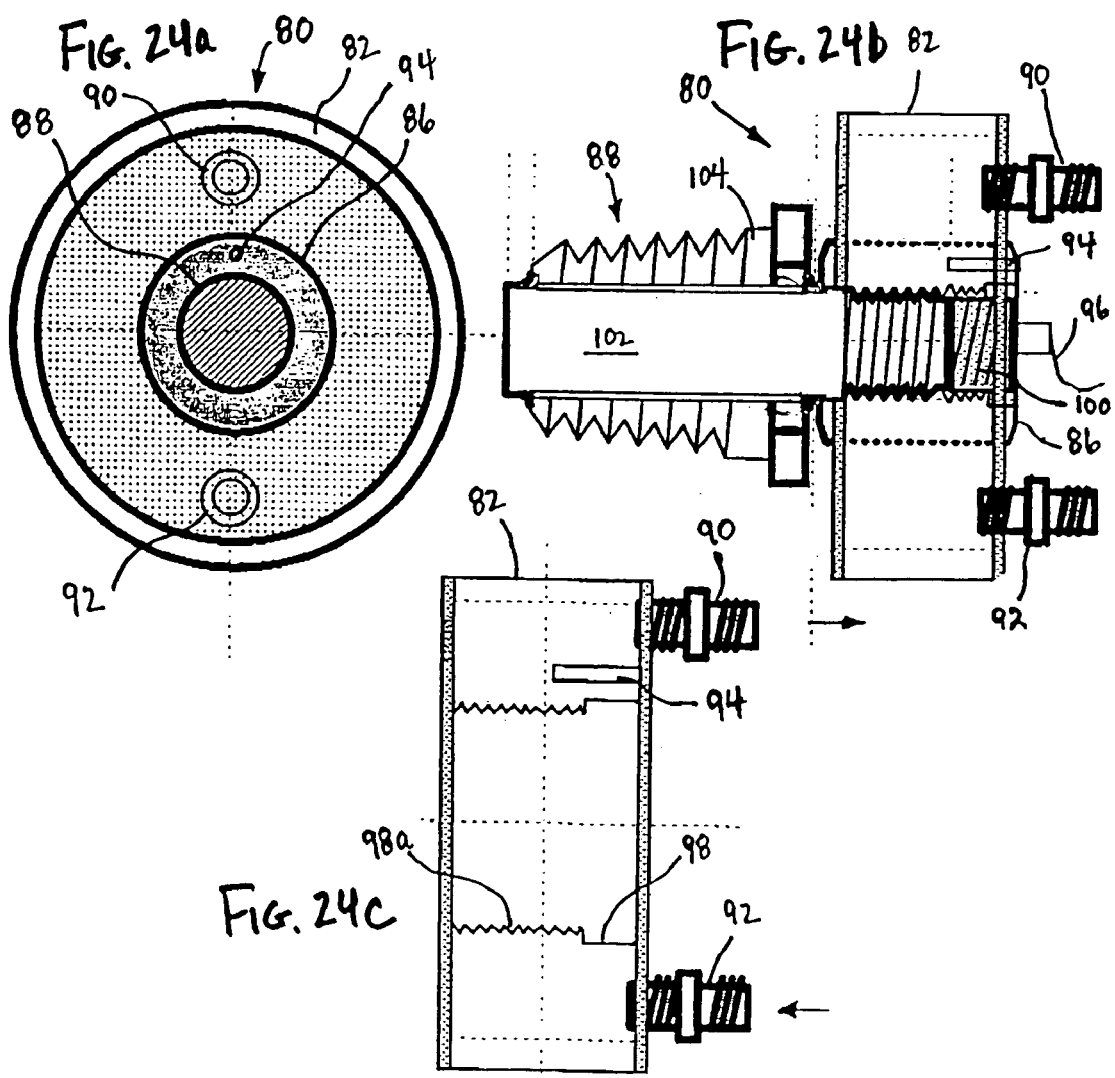
FIGS. 24a, 24b and 24c show different sectional views of another embodiment of a coupler for connecting an ultrasound wave generating or receiving transducer to a bubble column reactor for use in the ultrasound analysis of slurries in accordance with another aspect of the present invention.

Referring to FIGS. 24a, 24b and 24c, there are shown various sectional views of a coupler 80 for connecting a transducer 100 to an autoclave reactor of the bubble column type for the ultrasound analysis of slurries in accordance with another embodiment of the present invention. The coupler 80 shown in FIGS. 24a, 24b and 24c is particularly adapted for the ultrasound analysis of slurries at high temperatures and high pressures. As in the previously described embodiment, coupler 80 includes a hollow, disc-shaped cooling chamber 82 having a generally circular lateral wall and flat, opposed end walls. Inserted through one of the cooling chamber's end walls is an adapter 88 for connecting the coupler 80 to a bubble column reactor in a sealed manner. Adapter 88 is similar in configuration and construction to adapter 50 shown in FIGS. 3 and 4 and described in detail above. Coupler 80 includes an aperture within the coupling chamber 82 within which is inserted an insert rod 86 as in the previously described embodiment which extends the length of the coupler. The aperture through the insert rod 86 is threaded 98a and indented 98 so as to threadably engage an end of adapter 88 and an end of a transducer 100 for securely positioning the adapter and transducer in intimate end-to-end contact also as in the previously described embodiment A second, flat end wall of the cooling chamber 82 has a pair of spaced apertures therein within which are threadably inserted a coolant inlet 90 and a coolant outlet 92 which allow a coolant to be circulated through the cooling chamber for removing heat from transducer 100 via insert rod 86. Disposed within the insert rod 86 is an elongated, linear thermowell 94 which is adapted for receiving a thermocouple for measuring the temperature within the insert rod immediately adjacent to transducer 100. An electrical lead 96 is connected to and extends from transducer 100 for providing appropriate input signals to the transducer for generating an ultrasound signal or for transmitting and processing an ultrasound signal received by the transducer.

Figure 25:
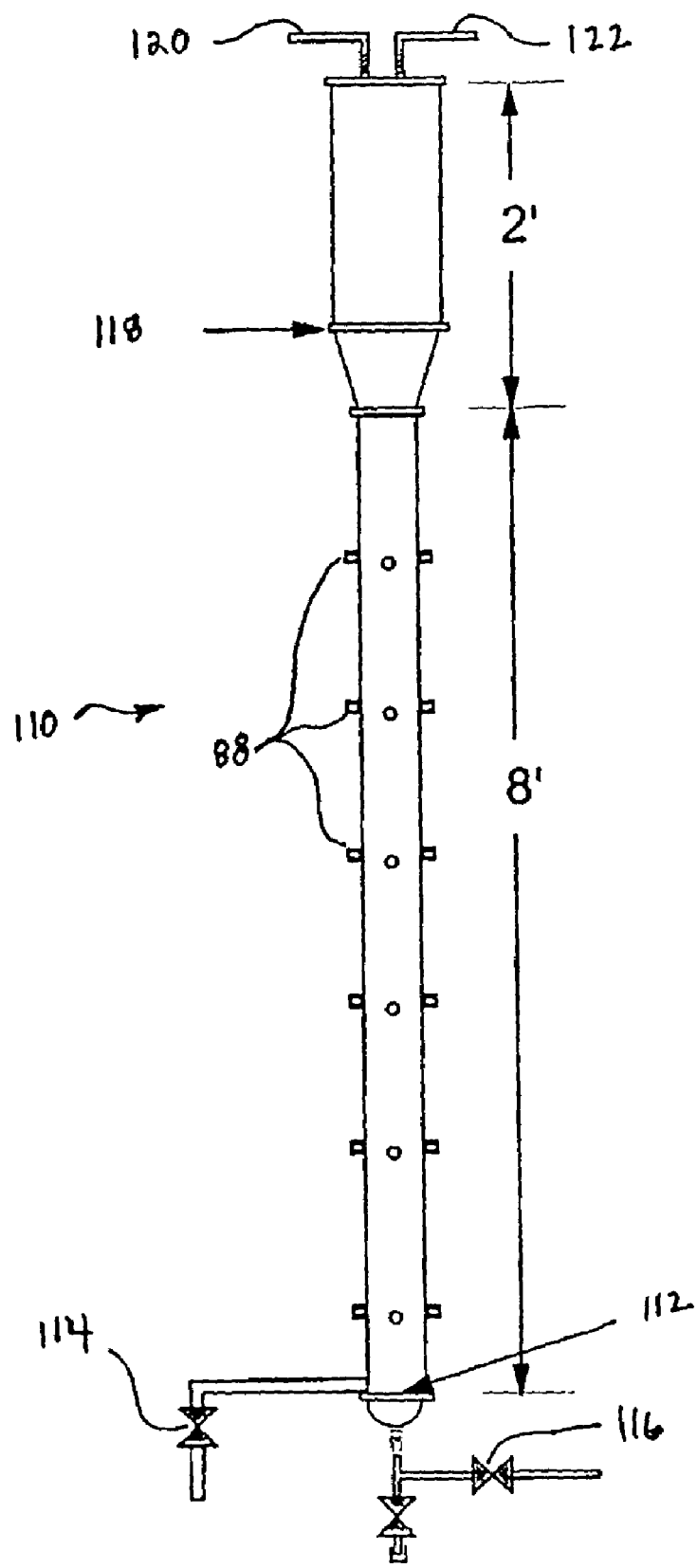
FIG. 25 is a simplified schematic diagram of another arrangement for conducting ultrasound analysts of slurries using a bubble column reactor in accordance with another embodiment of the present invention which is particularly adapted for slurry analysis at high temperatures and pressures.

Referring to FIG. 25, there is shown a schematic diagram of a stainless steel bubble chamber reactor 110 incorporating plural couplers 80 as shown in FIGS. 24a, 24b and 24c for conducting high temperature and high pressure ultrasound analysis of a slurry in accordance with this embodiment of the invention. The bubble chamber reactor 110 includes at its lower end a gas distributor plate 112 and a gas inlet 116. Also connected to the lower end of the bubble chamber reactor 110 is a transfer line 114. Disposed in an upper portion of the bubble chamber reactor 110 is an expansion zone 118. A gas outlet 120 and a compressed air inlet 122 are connected to an upper end portion of the bubble chamber reactor 110.

Coupler 80 including adapter 88 can be installed using modified ¾" NPT female connectors welded to the slurry bubble column reactor 110 for obtaining high temperature/high pressure ultrasonic measurements of the density and particle size distribution of a slurry. The length/taper ratio and configuration of the female connectors were modified to accommodate the ultrasonic adapter of the present invention. These modifications allow the adapters to be directly exposed to the slurry within the bubble column reactor 110, with minimum ultrasonic wave travel distance to/from the slurry, while maintaining the desired pressure within the bubble column reactor. Each adapter 88 maintains the smooth transmission of ultrasonic signals through the parallel contact surfaces of the adapter 88 and transducer 100. A ¹⁄₁₀₀₀" gap was provided between the end of an inner coupling rod 102 of the adapter 88 and an outer reducing bushing 104. This gap maximizes ultrasonic signal transmission and minimizes heat transfer from the wall of the bubble column reactor to the transducer. This gap can also reduce signal interference of the ultrasonic signal as it travels through the wall of the bubble chamber reactor to the adapter 88, and then to transducer 100. Cooling chamber 82 provides sufficient cooling and perfect contact between adapter 88 and transducer 100, with a thermocouple (which is not shown for simplicity) disposed within the thermowell 94 for temperature measurement of transducer 100. Bubble chamber reactor 110 is 4"×10' and includes a Drakeol-nitrogen system. The stainless steel bubble column reactor 110 has an internal diameter of 10 cm and a height of 305 cm. The bubble column reactor 110 has six sets of ultrasonic adapters 88, a cooling chamber assembly, transducers, and modified welding NPT female connectors installed in the reactor, although these latter elements are not shown in FIG. 25 for simplicity. The cooling chamber assemblies are arranged in pairs, with each pair within an assembly disposed 180° relative to one another about the bubble column reactor 110. Thus, an ultrasonic wave travels from an emitting transducer through the slurry medium and is received by an ultrasonic transducer receiver on an opposed portion of the reactor. The embodiment of the invention shown in FIGS. 24a, 24b and 24c, as well as in FIG. 25, has been tested up to 200° C., a pressure of 214 psi, and up to 11 cm/sec of gas velocity within the bubble column reactor. Experiments have been conducted in batch-mode operation (stationary liquid, Drakeol, and continuous flow of gas, nitrogen). The feed nitrogen was metered with a mass flow meter, passed through a preheater to the gas distributor, and then directed into the main column of the bubble column reactor 110. The bubble column reactor 110 has a perforated-plate gas distributor 112 with 25×1 mm diameter apertures disposed along the center of the bubble column reactor 110.

All ultrasonic measurements were taken with the inventive arrangement shown in FIGS. 24a, 24b, 24c and 25 at 20" and 32" above the gas distributor within the bubble column reactor 110. Experiments were conducted at temperatures of 20° C. and 200° C., at pressures of 14.7, 114.7 and 214.7 psig, and at superficial gas velocities of up to 11 cm/sec with the Drakeol oil (C16-C38 saturated hydrocarbon liquid) as the liquid-phase medium and nitrogen as the gas-phase medium.

FIG. 26 graphically shows the change in the amplitude ratio ($A/A_0$) of transmitted ultrasonic signals within the bubble column reactor 110 obtained 20" (50 cm) above the gas distributor as a function of gas velocity under two different pressures at 20° C. As shown in FIG. 26, the $A/A_o$ ratio reduces sharply under 14.7 psi. However, this ratio decreases slowly under 214.7 psig. These results suggest that the hydrodynamics are different under high pressure conditions versus low pressure conditions.

FIG. 27 graphically illustrates the effects of superficial gas velocity on ultrasonic signal transit time under different pressures of 14.7 and 214.7 psig at 20° C. The results were obtained 20" above the gas distributor. Transit time does not have an apparent correlation with gas velocity, as transit time is approximately 96 μsec at 214.7 psig and 96.5 usec at 14.7 psig. These results suggest that the transit time of an ultrasonic signal is not affected by the nitrogen flow rate within the bubble column reactor 110 obtained 20" above the gas distributor.

FIG. 28 graphically shows the change in the amplitude ratio ($A/A_0$) of transmitted ultrasonic signals within the bubble column reactor 110 obtained 20" above the gas distributor as a function of gas velocity at pressures of 114.7 and 214.7 psig at 200° C. The $A/A_0$ ratio reduces slowly at 14.7 psig. However, this ratio decreases more slowly at 214.7 psig. These results further suggest that the hydrodynamics are different under high pressure conditions versus under low pressure conditions.

FIG. 29 graphically illustrates the effects of superficial gas velocity on transit time at pressures of 114.7 and 214.7 psig at 200° C. These results were obtained 20" above the gas distributor. Transit time does not have an apparent correlation with the gas velocity. Transit time is approximately 143 usec for both pressures. These results suggest that the transit time of an ultrasonic signal is not affected by nitrogen flow rate or by the pressure within the bubble column reactor. These results further indicate that the inventive ultrasonic adapter and cooling chamber combination of the present invention could provide accurate ultrasonic measurements at temperatures as high as 200° C., pressures as high as 214 psig, and gas velocities as high as 11 cm/sec.

The ultrasound arrangement of the present invention can be used for solid and gas concentration measurements, solid particle distribution measurements in a two- or three-phase reactor under high temperatures and pressures. This invention is also adapted for use in measuring phase transitions (gas-liquid-solid transitions) that generally occur in $CO_2$ hydrate or methane hydrate under low temperature and high pressure conditions. This invention can also be used in ultrasonic liquid level measurements in elevated temperatures and pressures, as well as to measure the cooling medium in a nuclear reactor. Finally, the present invention can be used for most ultrasonic measurements under high/low temperature conditions and high pressure conditions.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for measuring the concentration and/or particle size distribution of a slurry, said apparatus comprising:
    a sealed container holding the slurry for applying elevated heat and pressure to the slurry, wherein the sealed container has an inner and outer wall;
    first and second transducers for respectively transmitting and receiving ultrasonic signals; and
    a first isolating coupler connecting said first transducer to a first portion of a lateral wall of said container and a second isolating coupler connecting said second transducer to a second portion of the lateral wall of said container for respectively transmitting an ultrasonic signal emitted by said first transducer through the slurry and transmitting an ultrasonic signal exiting said container to said second transducer, wherein the ultrasonic signal undergoes changes in transiting the slurry, with said changes providing a measure of the slurry's concentration and/or particle size distribution, and wherein said first and second couplers respectively isolate said first and second transducers from the heat and pressure in said sealed container.

2. The apparatus of claim 1 further comprising a source of coolant connected to said first and second couplers for maintaining said first and second transducers at an ambient temperature.

3. The apparatus of claim 2 wherein each of said first and second couplers is a generally closed housing disposed about said first and second transducers, respectively.

4. The apparatus of claim 3 wherein each of said housings is in the general form of a disc having a peripheral lateral wall connected to said source of coolant and first and second opposed end walls respectively coupled to said sealed container and to a respective transducer.

5. The apparatus of claim 3 wherein each of said housings is in the general form of a disc having a generally circular lateral wall and first and second opposed end walls respectively coupled to said sealed container and to a respective transducer, and wherein said second opposed end wall is further connected to said source of coolant.

6. The apparatus of claim 1 further comprising a series of vertical baffles positioned along the inner wall of the sealed container.

7. The apparatus of claim 1 further comprising a stirrer having one or more propeller blades extending into the sealed container.

8. The apparatus of claim 1 further comprising a gas line disposed in the sealed container to discharge gas bubbles in the slurry.

9. An apparatus for measuring the concentration and/or particle size distribution of a slurry, said apparatus comprising:
    a sealed container holding the slurry for applying elevated heat and pressure to the slurry;
    first and second transducers for respectively transmitting and receiving ultrasonic signals;
    a first isolating coupler connecting said first transducer to a first portion of a lateral wall of said container and a second isolating coupler connecting said second transducer to a second portion of the lateral wall of said container for respectively transmitting an ultrasonic signal emitted by said first transducer through the slurry and transmitting an ultrasonic signal exiting said container to said second transducer, wherein the ultrasonic signal undergoes changes in transiting the slurry, with said changes providing a measure of the slurry's concentration and/or particle size distribution, and wherein said first and second couplers respectively isolate said first and second transducers from the heat and pressure in said sealed container;
    a source of coolant connected to said first and second couplers for maintaining said first and second transducers at an ambient temperature, wherein each of said first and second couplers is a generally closed housing disposed about said first and second transducers, respectively; and wherein each of said first and second couplers includes a respective adapter for connecting a respective closed housing to said sealed container, wherein each adapter comprises an inner coupling rod and an outer bushing concentrically disposed about said rod in a spaced manner and connected to said rod.

10. The apparatus of claim 9 wherein each of said inner coupling rods has a first end disposed within said sealed container and a second opposed end disposed in a coupler and in contact with an associated transducer, and wherein a first coupling rod transmits an ultrasonic signal emitted by said first transducer into said container and a second coupling rod transmits an ultrasonic signal having transited the slurry to said second transducer.

11. The apparatus of claim 10 wherein the first and second ends of each of said coupling rods are parallel.

12. The apparatus of claim 9 wherein each of said coupling rods and bushings is comprised of stainless steel.

13. The apparatus of claim 9 wherein adjacent ends of said coupling rod and said bushing are connected together by spot weldments, and wherein a closed annular gap is disposed between said coupling rod and said bushing for limiting thermal transmission and ultrasonic signal interference between said sealed container and a transducer.

14. The apparatus of claim 9 wherein a distal end of said coupling rod includes a first threaded portion coupled to said closed housing, and wherein a proximal end of said bushing includes a second threaded portion coupled to the lateral wall of said sealed container.

15. The apparatus of claim 14 wherein said second threaded portion is tapered.

16. The apparatus of claim 15 wherein each of said first and second transducers includes a respective third threaded portion, and wherein each of said third threaded portions is coupled to a respective one of said closed housings.

17. The apparatus of claim 16 wherein each of said closed housings includes a respective threaded slot extending between the first and second opposed end walls of said closed housing, and wherein a second threaded portion of a bushing and a third threaded portion of a transducer are inserted in and engage a threaded slot in each of said closed housings.

18. An apparatus for measuring the concentration and/or particle size distribution of a slurry, said apparatus comprising:

a sealed container holding the slurry for applying elevated heat and pressure to the slurry, wherein the sealed container has an inner and outer wall;

first and second transducers for respectively transmitting and receiving ultrasonic signals; and a first isolating coupler connecting said first transducer to a first portion of a lateral wall of said container and a second isolating coupler connecting said second transducer to a second portion of the lateral wall of said container for respectively transmitting an ultrasonic signal emitted by said first transducer through the slurry and transmitting an ultrasonic signal exiting said container to said second transducer, wherein the ultrasonic signal undergoes changes in transiting the slurry, with said changes providing a measure of the slurry's concentration and/or particle size distribution, and wherein said first and second couplers respectively isolate said first and second transducers from the heat and pressure in said sealed container; and wherein each of said couplers includes a respective thermowell disposed adjacent a respective transducer for receiving a thermocouple for determining an operating temperature of the transducer.

19. Apparatus for directing an ultrasonic signal through a slurry or receiving an ultrasonic signal transmitted through a slurry for determining characteristics of the slurry, said apparatus comprising:

an autoclave reactor containing the slurry and maintaining the slurry at elevated temperatures and pressures;

a transducer for directing an ultrasonic signal into said autoclave reactor and through the slurry or for receiving an ultrasonic signal exiting said autoclave reactor after transiting the slurry; and a coupler for connecting said transducer to said autoclave reactor and isolating said transducer from the elevated temperatures and pressures within said autoclave reactor, said coupler including means for circulating a coolant about said transducer, an acoustic member in contact with the transducer for transmitting an ultrasonic signal emitted by said transducer into said autoclave reactor or an ultrasonic signal exiting said autoclave reactor after transiting the slurry to said transducer, a connector attaching said acoustic member to said autoclave reactor for transmitting an ultrasonic signal into said autoclave reactor or receiving an ultrasonic signal exiting said autoclave reactor, wherein said connector and acoustic member are thermally isolated from one another for allowing said transducer to operate at ambient temperature and pressure.

* * * * *